Figure 1:
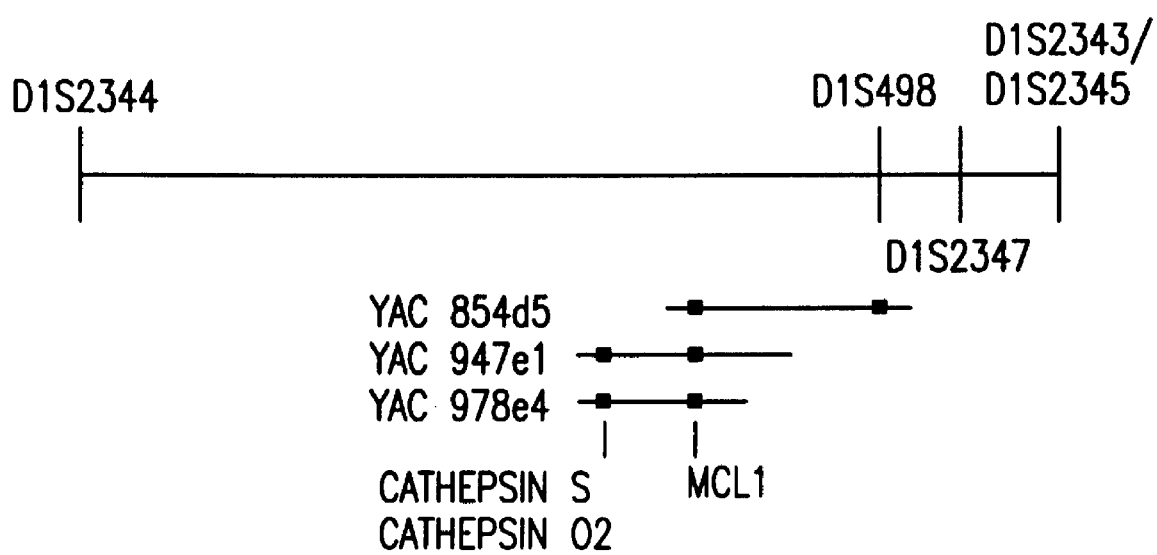

United States Patent [19]
Gelb et al.

[11] Patent Number: 5,830,850
[45] Date of Patent: Nov. 3, 1998

[54] METHODS FOR THE TREATMENT OF BONE RESORPTION DISORDERS, INCLUDING OSTEOPOROSIS

[75] Inventors: Bruce D. Gelb, Dobbs Ferry, N.Y.; Harold Chapman, Newton, Mass.; Robert J. Desnick, New York, N.Y.

[73] Assignees: Mount Sinai School of Medicine of the City of New York, New York, N.Y.; Brigham and Women's Hospital, Boston, Mass.

[21] Appl. No.: 704,473

[22] Filed: Aug. 28, 1996

[51] Int. Cl.[6] ...................................................... A61K 48/00
[52] U.S. Cl. ................................. 514/2; 436/501; 514/44; 935/88
[58] Field of Search .................................. 435/69.1, 810; 436/501; 514/2, 44; 935/88

[56] References Cited

U.S. PATENT DOCUMENTS

| | | | |
|---|---|---|---|
| 4,873,191 | 10/1989 | Wagner et al. | 435/172.3 |
| 5,158,936 | 10/1992 | Krantz et al. | 514/19 |
| 5,374,623 | 12/1994 | Zimmerman et al. | 514/17 |
| 5,399,349 | 3/1995 | Paunescu et al. | 424/195.1 |
| 5,460,959 | 10/1995 | Mulligan et al. | 435/172.3 |
| 5,486,623 | 1/1996 | Zimmerman et al. | 549/417 |
| 5,501,969 | 3/1996 | Hastings et al. | 435/240.2 |
| 5,525,623 | 6/1996 | Spear et al. | 514/423 |
| 5,550,138 | 8/1996 | Sodhae et al. | 514/361 |

FOREIGN PATENT DOCUMENTS

| | | |
|---|---|---|
| WO 88/04300 | 6/1988 | WIPO . |
| WO 88/09810 | 12/1988 | WIPO . |
| WO 89/10134 | 11/1989 | WIPO . |
| WO 90/11364 | 10/1990 | WIPO . |
| WO 95/23222 | 8/1995 | WIPO . |

OTHER PUBLICATIONS

Bossard, M.J. et al., 1996, "Proteolytic Activity of Human Osteoclast Cathepsin K", J of Biol Chemistry 271:12517–12524.

Brömme, D. et al., 1996, "Human Cathepsin O2, a Matrix Protein–degrading Cysteine Protease Expressed in Osteoclasts", J of Biol Chemistry 271:2126–2132.

Drake, F. et al., 1996, "Cathepsin K, but Not Cathepsins B, L, or S, Is Abundantly Expressed in Human Osteoclasts", J of Biol Chemistry 271:12511–12516.

Gelb, B. et al., 1996, "Pycnodysostosis: Refined Linkage and Radiation Hybrid Analyses Reduce the Critical Region to 2 cM at 1q21 and Map Two Candidate Genes", Human Genet. 98:141–144.

Riese, R. et al., 1996, "Essential Role for Cathepsin S in MHC Class II–Associated Invariant Chain Processing and Peptide Loading", Immunity 4:357–366.

Bromme, and Okamoto, 1995, "Human Cathepsin O2, a Novel Cysteine Protease Highly Expressed in Osteoclastomas and Ovary Molecular Cloning, Sequencing and Tissue Distribution", Biol Chem Hoppe–Seyler 376:379–386.

Debari, K. et al., 1995, "An Ultrastructural Evaluation of the Effects of Cysteine–Proteinase Inhibitors on Osteoclastic Resorptive Funtions", Calcif. Tissue Int. 56:566–570.

(List continued on next page.)

*Primary Examiner*—Ardin H. Marschel
*Attorney, Agent, or Firm*—Pennie & Edmonds LLP

[57] ABSTRACT

The present invention relates to methods and compositions for the amelioration of symptoms caused by bone resorption disorders, including but not limited to osteoporosis, arthritides and periodontal disease, and damage caused by macrophage-mediated inflammatory processes. In one embodiment, the methods and compositions of the invention include methods and compositions for the specific inhibition of cathepsin K activity. In an additional embodiment, the methods and compositions of the invention include methods and compositions for the specific inhibition of cathepsin K activity coupled with specific inhibition of at least a second activity involved in the bone resorption and/or macrophage-mediated inflammatory processes. In a particular embodiment, the methods and compositions of the invention include methods and compositions for the specific inhibition of cathepsin K and cathepsin S activity.

5 Claims, 6 Drawing Sheets

OTHER PUBLICATIONS

Gelb, B.D. et al., 1995, "Linkage of Pycnodysostosis to Chromosome 1q21 by Homozygosity Mapping", Nature Genet. 10:235–237.

Horinouchi, K. et al., 1995, "Acid Sphingomyelinase Deficient Mice: A Model of Types A and B Niemann–Pick Disease", Nature Genetics 10:288–293.

Inaoka, T. et al., 1995, "Molecular Cloning of Human cDNA for Cathepsin K: Novel Cysteine Proteinase Predominantly Expressed in Bone", Biochem. Biophys. Res. Commun. 206:89–96.

Li, Y. et al., 1995, "Cloning and Complete Coding Sequence of a Novel Human Cathepsin Expressed in Giant Cells of Osteoclastomas", J. Bone Miner. Res. 10:1197–1202.

Munger, J. et al., 1985, "Lysosomal Processing of Amyloid Precursor Protein to Aβ Peptides: A Distinct Role for Cathepsin S", Biochem. J. 311:299–305.

Otterbach, and Stoffel, 1995, "Acid Sphingomyelinase–Deficient Mice Mimic the Neurovisceral Form of Human Lysosomal Storage Disease (Niemann–Pick Disease)", Cell 81:1053–1061.

Palmer, J. et al., 1995, "Vinyl Sulfones as Mechanism–Based Cysteine Protease Inhibitors", J. Med. Chem. 38:3193–3196.

Polymeropoulos, M. et al., 1995, "The Gene for Pycnodysostosis Maps to Human Chromosome 1 cen–q21", Nature Genet. 10:238–239.

Richard, I. et al., 1995, "Mutations in the Proteolytic Enzyme Calpain 3 Cause Limb–Girdle Muscular Dystrophy Type 2A", Cell 81:27–40.

Rousseau, F., 1995, "Stop Codon FGFR3 Mutations in Thanatophoric Dwarfism Type 1", Nature Genetics 10:11–12.

Shi, G. et al., 1995, "Molecular Cloning of Human Cathepsin O, a Novel Endoproteinase and Homologue of Rabbit OC2", FEBS Letters 357:129–134.

Sim, and Doorn, 1995, "Radiographic Measurement of Bone Mineral: Reviewing Dual Energy X–Ray Absorptiometry", Austral. Phys. Eng. Sci. Med. 18:65–80.

Sohrabji, F. et al., 1995, "Identification of a Putative Estrogen Response Element in the Gene Encoding Brain–Derived Neurotrophic Factor", PNAS U.S.A. 92:11110–11114.

Goto, T., 1994, "Localization of Cathepsins B, D, and L in the Rat Osteoclast by Immuno–Light and –Electron Microscopy", Histochemistry 101:33–40.

Kirschke, H. and Wiederanders, B., 1994, "Cathepsin S and Related Lysosomal Endopeptidases", Methods in Enzymology: 244:500, Academic Press, NY.

Krane and Simon, 1994, in Scientific American Medicine, Rubenstein, E. & Felderman, D.D., ed., Scientific American, Inc., New York, pp. 1–26.

Li, Y.P. et al., 1994, "Cloning and Characterization of a Novel Cathepsin from Human Osteoclasts" (Abstract), Mol. Biol. Cell 5:335a.

Shi, G. et al., 1994, "Human Cathepsin S: Chromosomal Localization, Gene Structure, and Tissue Distribution", J. Biol. Chem. 269:11530–11536.

Tezuka, K. et al., 1994, "Molecular Cloning of a Possible Cysteine Proteinase Predominantly Expressed in Osteoclasts", J. Biol. Chem. 269:1106–1109.

Velasco, G. et al., 1994, "Human Cathepsin O", J. Biol. Chem. 269:27136–27142.

Wagner, R., 1994, "Gene Inhibition Using Antisense Oligonucleotides", Nature 372:333–335.

Blair, H. et al., 1993, "Recent Advances Toward Understanding Osteoclast Physiology", Clin. Orthop. 294:7–22.

Cauley, J. et al., 1993, "Effects of Thiazide Diuretic Therapy on Bone Mass, Fractures, and Falls", Ann. Intern. Med. 118:666–673.

Chauhan, S. et al., 1993, "Cloning, Genomic Organization, and Chromosomal Localization of Human Cathepsin L", J. Biol. Chem. 268:1039–1045.

Dietz, H. et al., 1993, "The Skipping of Constitutive Exons in Vivo Induced by Nonsense Mutations", Science 259:680–682.

Gong, Q. et al., 1993, "Characterization of the Cathepsin B Gene and Multiple mRNAs in Human Tissues: Evidence for Alternative Splicing of Cathepsin B Pre–mRNA", DNA and Cell Biol. 12:299–309.

Horowitz, M., 1993, "Cytokines and Estrogen in Bone: Anti–Osteoporotic Effects", Science 260:626–627.

Kakegawa, H. et al., 1993, "Participation of Cathepsin L on Bone Resorption", FEBS 321:247–250.

Wood, S. et al., 1993, "Simple and Efficient Production of Embryonic Stem Cell–Embryo Chimeras by Coculture", PNAS USA 90:4582–4584.

Bradley, A. et al., 1992, "Modifying the Mouse: Design and Desire", Bio/Technology 10:534–539.

Chapuy, M. et al., 1992, "Vitamin $D_3$ and Calcium to Prevent Hip Fractures in Elderly Women", N. Engl. J. Med. 327:1637–1642.

Christiansen, C., 1992, "Prevention and Treatment of Osteoporosis: A Review of Current Modalities" Bone 13 (Supp.1):S35–S39.

Everts, V. et al., 1992, "Degradation of Collagen in the Bone–Resorbing Compartment Underlying the Osteoclast Involves Both Cysteine–Proteinases and Matrix Metalloproteinasses", J. Cell. Physiol. 150:221–231.

Helene, C. et al., 1992, "Control of Gene Expression by Triple Helix–Forming Oligonucleotides", Ann. NY Acad. Sci. 660:27–36.

Maher, L.J., 1992, "DNA Triple–Helix Formation: An Approach to Artificial Gene Repressors?", Bioassays 14:807–815.

Page A. et al., 1992, "Human Osteoclastomas Contain Multiple Forms of Cathepsin B", Biochem Biophys. Acta 1116:57–66.

Riggs, B. et al., 1992, "The Prevention and Treatment of Osteoporosis", N. Engl. J. Med. 327:620–627.

Rodan, G., 1992, "Introduction to Bone Biology", Bone 13:S3–S6.

Shi, G. et al., 1992, "Molecular Cloning and Expression of Human Alveolar Macrophage Cathepsin S, an Elastinolytic Cysteine Protease", J. Biol. Chem. 267:7258–7262.

Greenspan, A., 1991, "Sclerosing Bone Dysplasias—a Target–Site Approach", Skeletal Radiol. 20:561–583.

Helene, C., 1991, "The Anti–Gene Strategy: Control of Gene Expression by Triplex–Forming–Oligonucleotides", Anti–Cancer Drug Design 6:569–584.

Kim, H. et al., 1991, "Problems Encountered in Detecting a Targeted Gene by the Polymerase Chain Reaction", Gene 103:227–233.

Prince, R. et al., 1991, "Prevention of Postmenopausal Osteoporosis", N. Engl. J. Med. 325:1189–1195.

Avioli, L. et al., 1990, in Metabolic Bone Disease and Clinical Related Disorders, Avioli, L.V. and Crane eds., Saunders Co. Philadelphia, p. 397.

Ferrara et al., 1990, "Gene Structure of Mouse Cathepsin B", FEBS Letters 273:195–199.

Hock, J.M. et al., 1990, "Anabolic Effect of Human Synthetic Parathyroid Hormone–(1–34) Depends on Growth Hormone", Endocrinology 127:1804–1810.

Sarver, N. et al., 1990, "Ribozymes as Potential Anti–HIV–1 Therapeutic Agents", Science 247:1222–1225.

Storm, T. et al., 1990, "Effect of Intermittent Cyclical Etidronate Therapy on Bone Mass and Fracture Rate in Women with Postmenopausal Osteoporosis", N. Engl. J. Med. 322:1265–1271.

Wagner, E., 1990, "On Transferring Genes into Stem Cells and Mice", EMBO J. 9:3025–3032.

Watts, N. et al., 1990, "Intermittent Cyclical Etidronate Teatment of Postmenopausal Osteoporosis", N. Engl. J. Med. 323:73–79.

Barribault, H. et al., 1989, "Embryonic Stem Cell Culture and Gene Targeting in Transgenic Mice", Mol. Biol. Med. 6:481–492.

Capecchi, M., 1989, "Altering the Genome by Homologous Recombination", Science 244:1288–1292.

Cappecchi, M., 1989, "The New Mouse Genetics: Altering the Genome by Gene Targeting", Trends in Genet. 5:70–76.

Frohman, M. et al., 1989, "Cut, Paste, and Save: New Approaches to Altering Specific Genes in Mice", Cell 56:145–147.

Gordon, J., 1989, "Transgenic Animals", Int'l Rev. Cytol. 115:171–229.

Kirshke, H. et al., 1989, "Cathepsin S from Bovine Spleen", Biochem. J. 264:467–473.

Lavitrano, M. et al., 1989, "Sperm Cells as Vectors for Introducing Foreign DNA into Eggs: Genetic Transformation of Mice", Cell 57:717–723.

Letsinger, R. et al., 1989, "Cholesterol–Conjugated Oligonecleotides: Synthesis, Properties and Activity as Inhibitors of Replication of Human Immunodeficiency Virus in Cell Culture", PNAS USA 86:6553–6556.

Melton, L.J. and Riggs, B.L., 1989, in Clinical Disorders of Bone and Mineral Metabolism, Kleerekoper, M. and Krane, S.M. eds., Mary Ann Liebert, NY, p. 145.

Sedivy, J. et al., 1989, "Positive Genetic Selection for Gene Disruption in Mammalian Cells by Homologous Recombination", PNAS USA 86:227–231.

Thompson, S. et al., 1989, "Germ Line Transmission and Expression of a Corrected HPRT Gene Produced by Gene Targeting in Embryonic Stem Cells", Cell 56:313–321.

Everts, V et al., 1988, "Effects of the Proteinase Inhibitors Leupeptin and E–64 on Osteoclastic Bone Resorption", Calcif. Tissue Int. 43:172–178.

Haseloff and Gerlach, 1988, "Simple RNA Enzymes with New and Highly Specific Endoribonuclease Activities", Nature 334:585–591.

Jaenisch, R., 1988, "Transgenic Animals", Science 240:1468–1474.

Kim, H. et al., 1988, "Recombinant Fragment Assay for Gene Targeting Based on the Polymerase Chain Reaction", Nucl. Acids Res. 16:8887–8903.

Krol, A. et al., 1988, "Modulation of Eukaryotic Gene Expression by Complementary RNA or DNA Sequences", Biotechniques 6:958–976.

Mansour, S. et al., 1988, "Disruption of the Proto–Oncogene int–2 in Mouse Embryo–Derived Stem Cells: A General Strategy for Targeting Mutations to Non–Selectable Genes", Nature 336:348–352.

Sarin, P. et al., 1988, "Inhibition of Acquired Immunodeficiency Syndrome Virus by Oligodeoxynucleoside Methylphosphonates", PNAS USA 85:7448–7451.

Stein, C.A. et al., 1988, "Physiochemical Properties of Phosphorothioate Oligodeoxynucleotides", Nucl. Acids Res. 16:3209–3221.

Zon, G., 1988, "Oligonucleotide Analogues as Potential Chemotherapeutic Agents", Pharm. Res. 5:539–549.

Gautier, G. et al., 1987, "α–DNA IV: α–anomeric and β–anomeric Tetrathymidylates Covalently Linked to Intercalating Oxazolopyridocarbazole. Synthesis, Physicochemical Properties and Poly (rA) Binding", Nucl. Acids Res. 15:6625–6641.

Inoue, H. et al., 1987, "Syntheis and Hybridization Studies on Two Complementary Nona(2'–O–methyl)ribonucleotides", Nucl. Acids Res. 15:6131–6148.

Inoue, H. et al., 1987, "Sequence–dependent Hydrolysis of RNA Using Modified Oligonucleotide Splints and RNase H", FEBS Letters 215:327–330.

Kaufman and Murtha, 1987, "Translational Control Mediated by Eucaryotic Initiation Factor–2 Is Restricted to Specific mRNAs in Transfected Cells". Mol. Cell. Biol. 7:1568.

Kirshke and Barrett, 1987, in Lysozomes: Their Role in Protein Breakdown, Glaumann, H. & Ballard, F.J. eds., Academic Press, London, pp. 193–238.

Lemaitre, M. et al., 1987, "Specific Antirviral Activity of a Poly (L–lysine)–Conjugated Oligodeoxyribonucleotide Sequence Complementary to Vesicular Stomatitis Virus N Protein mRNA Initiation Site", PNAS 84:648–652.

Thomas and Capecchi, 1987, "Site–Directed Mutagenesis by Gene Targeting in Mouse Embryo–Derived Stem Cells", Cell 51:503–512.

Been and Cech, 1986, "One Binding Site Determines Sequence Specificity of Tetrahymena Pre–rRNA Self–Splicing, Trans–Splicing, and RNA Enzyme Activity", Cell 47:207–216.

Chan, S. et al., 1986, "Nucleotide and predicted amino acid sequences of cloned human and mouse preprocathepsin B cDNAs", PNAS USA 83:7721–7725.

Gossier A. et al., 1986, "Transgenesis by Means of Blastocyst–Derived Embryonic Stem Cell Lines", PNAS USA 83:9065–9069.

Riggs and Melton, 1986, "Medical Progess—Involutional Osteoporosis", N. Engl. J. Med. 314:1676.

Robertson, H.D. et al., 1986, "Clues about RNA Enzymes", Nature 322:445–448.

Zaug, A. et al., 1986, "The *Tetrahymena* Ribozyme Acts like and RNA Restriction Endonuclease", Nature 324:429–433.

Zaug and Cech, 1986, "The Intervening Sequence RNA of *Tetrahymena* is an Enzyme", Science 231:470–475.

Everts, V. et al., 1985, "Phagocytosis of Bone Collagen by Osteoclasts in Two Cases of Pycnodysostosis", Calcif. Tissue Int. 37:25–31.

Small, J. et al., 1985, "Analysis of a Transgenic Mouse Containing Simian Virus 40 and v–myc Sequences", Moll. Cell Biol. 5:642–648.

Van der Putten, H. et al., 1985, "Efficient Insertion of Genes into the Mouse Germ Line via Retroviral Vectors", PNAS U.S.A. 82:6148–6152.

Bradley, A. et al., 1984, "Formation of Germ–Line Chimaeras from Embryo–Derived Teratocarcinoma Cell Lines", Nature 309:255–256.

Delaisse, J. et al., 1984, "In Vivo and In Vitro Evidence for the Involvment of Cysteine Proteinasses in Bone Resorption", Biochem. and Biophys. Res. Commun. 125:441–447.

Zaug, A. et al., 1984, "A Labile Phosphodiester Bond at the Ligation Jucntion in a Circular Intervening Sequence RNA", Science 224:574–578.

Lo, C., 1983,"Transformation by Iontophoretic Microinjection of DNA: Multiple Integrations without Tandem Insertions", Mol. and Cell. Biol. 3:1803–1814.

Nagent de Deuxchaisnes, C., 1983, in Osteoporosis, a Multi–Disciplinary Problem, Royal Society of Medicine Int'l Congress and Symposium Series No.55, Academic Press, London, p. 291.

Bishop and Desnick, 1981, "Affinity Purification of α–Galactosidase A from Human Spleen, Placenta, and Plasma with Elimination of Pyrogen Contamination", J. of Biol. Chem. 256:1307–1316.

Brinster, R. et al., 1982, "Regulation of Metallothionein–Thymidine Kinase Fusion Plasmids Injected into Mouse Eggs", Nature 296:39–42.

Hunt, D.M. et al., 1982, "Haemoglobin Constant Spring has an Unstable α Messenger RNA", Brit J. of haematology 51:405–413.

Benoist and Chambron, 1981, "In Vivo Sequence Requirements of the SV40 Early Promoter Region", Nature 290:304–310.

Evans, M.J. et al., 1981, "Establishment in Culture of Pluripotential Cells from Mouse Embryos", Nature 292:154–156.

Liebhaber, S. et al., 1981, "Differentiation of the mRNA Transcripts Originating from the α1–and α2–Globin Loci in Normals and α–Thalassemics", J. Clin Invest 68:439–446.

Wager, M. et al., 1981, "Nucleotide Sequence of the Thymidine Kinase Gene of Herpes Simplex Virus Type 1", PNAS USA 78:1441–1445.

Delaisse, J. et al., 1980, "Inhibition of Bone Resorption in Culture by Inhibitors of Thiol Proteinases", Biochem. J. 192:365–368.

Yamamoto, T. et al., 1980, "Identification of a Functional Promoter in the Long Terminal Repeat of Rous Sarcoma Virus", Cell 22:787–797.

Clegg, B. et al., 1971, "Haemoglobin Constant Spring–A Chain Termination Mutant?", Nature 234:337–340.

Andren, L. et al., 1962, "Osteopetrosis Acro–Osteolytica", Acta Chir. Scand.124:496–507.

Albright, F. et al., 1941, "Postmenopausal Osteoporosis", JAMA 116:2465–2474.

Chen, C.G. et al., 1996, "Reduction in Gal–α1,3–Gal Epitope Expression in Transgenic Mice Expressing Human H–Transferase", Xenotransplantation 3:69–75.

Koike, C. et al., 1996, "Introduction of α(1,2)–fucosyltransferase and its Effect on α–Gal Epitopes in Transgenic Pig", Xenotransplantation 3:81–86.

Koike, c. et al., 1996, "Converting α–Gal Epitope of Pig into H Antigen", Transplantation Proceedings 28:553.

Sandrin MS et al., 1996 "Reduction of the Major Porcine Xenoantigen Galα(1,3)Gal by Expression of α(1,2)fucosyltransferase", Xenotransplantation 3:134–140.

Sharma, A. et al., 1996, "Reduction in the Level of Gal(α1, 3)Gal in Transgenic Mice and Pigs by the Expression of an α(1,2)fucosyltransferase", PNAS 93:7190–7195.

Saneshige et al., 1995, "Retinoic Acid Directly Stimulates Osteoclastic Bone Resorption and Gene Expression of Cathepsin K/OC–2", Biochem. J. 309:721–724.

FIG.6

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
    ( A ) LENGTH: 591 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

```
CCAACAAGCT    TATAAAATA    CAAAGAATTC    TGGAGCCTAT    GGCTTCCATT    ACATTATTCT       60

TTTATAGCCT    TTTATGTTCA    TTACCGCATC    CCAGAGGTGA    GAGTCAGACA    CAAATATGAA      120

AATAGGTTTC    AATGTTGGAG    AGGTAAATCC    TAACAGGAAA    GGGGTAGGAA    AAGATATAAT      180

CCCCCAATAT    TAAAATAAAG    ATATTGAAGA    AGAAGGATGG    GAGAGACTAG    GGCTGTGTCC      240
```

-continued

| | | | | | |
|---|---|---|---|---|---|
| TTCCTTTTAC | TCACCAAAAG | AGAAAGTAAG | CTCCTATTTG | AGTCAATAGA | TATTGAGGTC | 300 |
| TTGTTATTTG | CCACCAAAGA | CAGTCTTGTG | AGACTAAATA | GCTAGTAATT | CCCTACCCTG | 360 |
| GCACACATGC | TGCATACACA | CAGAAACACT | GCAAATCCAC | TGCCTCCTTC | CCTCCTCCCT | 420 |
| ACCCTTCCTT | CTCTCAGCAT | TTCTATCCCC | GCCTCCTCCT | CTTACCCAAA | TTTTCCAGCC | 480 |
| GATCACTGGA | GCTGAGTTCC | GCAATCCCGA | TGGAATAAAT | TCTAGCACCC | CTGATGGTGT | 540 |
| GCCCACACTT | TGCTGCCGAA | ACGAAGCCAG | ACAACAGATT | TCCATCAGCA | G | 591 |

( 2 ) INFORMATION FOR SEQ ID NO:2:

( i ) SEQUENCE CHARACTERISTICS:
        ( A ) LENGTH: 141 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

| | | | | | |
|---|---|---|---|---|---|
| GCGCACTCAC | AGTCGCAACC | TTTCCCCTTC | CTGACTTCCC | GCTGACTTCC | GCAATCCCGA | 60 |
| TGGAATAAAT | TCTAGCACCC | CTGATGGTGT | GCCCACACTT | TGCTGCCGAA | ACGAAGCCAG | 120 |
| ACAACAGATT | TCCATCAGCA | G | | | | 141 |

( 2 ) INFORMATION FOR SEQ ID NO:3:

( i ) SEQUENCE CHARACTERISTICS:
        ( A ) LENGTH: 148 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

| | | | | | |
|---|---|---|---|---|---|
| GAAACAAGCA | CTGGATTCCA | TATCCCACTG | CCCAAAACCG | CATGGTTCAG | ATTATCGCTA | 60 |
| TTGCAGCTTT | CATCATAATA | CACACCTTTG | CTCATAATAC | ACCTTTGC | TGCCGAAACG | 120 |
| AAGCCAGACA | ACAGATTTCC | ATCAGCAG | | | | 148 |

( 2 ) INFORMATION FOR SEQ ID NO:4:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

| | | | | | |
|---|---|---|---|---|---|
| ATTCGGCACG | AGCCGCAATC | CCGATGGAAT | AAATTCTAGC | ACCCTGATG | GTGTGCCCAC | 60 |
| ACTTTGCTGC | CGAAACGAAG | CCAGACAACA | GATTTCCATC | AGCAG | | 105 |

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
CAGATTTCCA TCAGCAG                                                        17

( 2 ) INFORMATION FOR SEQ ID NO:6:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:6:

GCATTTAAAG AGCTCTACCT AGGGTT                                              26

( 2 ) INFORMATION FOR SEQ ID NO:7:

( i ) SEQUENCE CHARACTERISTICS:
                ( A ) LENGTH: 33 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:7:

CAGAGAAATA TCACATATAA GTCAAACCCC AAT                                      33

( 2 ) INFORMATION FOR SEQ ID NO:8:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:8:

GCCGCAATCC CGATGGA                                                        17

( 2 ) INFORMATION FOR SEQ ID NO:9:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:9:

CCTTGAGGAT ATTGAAGGGA ACTTAG                                              26

( 2 ) INFORMATION FOR SEQ ID NO:10:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:10:

CCCCTGATGG TGTGCCCCA                                                      19

( 2 ) INFORMATION FOR SEQ ID NO:11:
```

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

CCCTTCCAAA GTGCATCGTT ACACT     25

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GGGGAGAAAA CTGGGGAAAC A     21

( 2 ) INFORMATION FOR SEQ ID NO:13:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

TCAGCAGGTA ACG     13

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CAACAAGGTG CCT     13

( 2 ) INFORMATION FOR SEQ ID NO:15:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GGACATGGCA AGT     13

( 2 ) INFORMATION FOR SEQ ID NO:16:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

AAATCAGGTA CTC    13

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GGGACAGGTG AGA    13

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

AGCAAAGGTA AGA    13

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

AAAACAGGTA ATG    13

( 2 ) INFORMATION FOR SEQ ID NO:20:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

CAAGGTGAAG T    11

( 2 ) INFORMATION FOR SEQ ID NO:21:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CTGTTTCCCT GCCAAATGGA AGAGTTTTCC CTAACTACAT TCTTCTGCAG GATGTGGGG    59

( 2 ) INFORMATION FOR SEQ ID NO:22:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

CATATGTAAC TGTAGACAGT CTATACAAGT ACTGACTATG CTTTGTTTAG GTGGATGAA    59

( 2 ) INFORMATION FOR SEQ ID NO:23:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

ATTTGCTTTA GTTCCCTGCT GATGCCTGGC CTCTTTCTTC TTTGTCTTAG ACCAGTGAA    59

( 2 ) INFORMATION FOR SEQ ID NO:24:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

ATAGAAAATG TAAACAGCAA AGATTGATAG TTTCTCTGTA TGCCTTTCAG GGTCAGTGT    59

( 2 ) INFORMATION FOR SEQ ID NO:25:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

TCATTGCCTA TTGCTTTGTC CTAGTCCTAT TACAATCTTG TTTCTTCCAG GAAGAGAGT    59

( 2 ) INFORMATION FOR SEQ ID NO:26:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

GGGTGACCCT TGGATTGCAT AGAGCCTCAC GCTGGTAGTT TGTATTCTAG GTGTGTATT    59

( 2 ) INFORMATION FOR SEQ ID NO:27:

( i ) SEQUENCE CHARACTERISTICS:
   ( A ) LENGTH: 59 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:27:

TGAATAAATA AACTGAGAGT ACTAAGTATT TTTCTTGATT GGTCTTACAG CTGGGGAGA    59

( 2 ) INFORMATION FOR SEQ ID NO:28:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:28:

CCCCCCCTCC CTTTTTTTCT TTNCAGG    27

METHODS FOR THE TREATMENT OF BONE RESORPTION DISORDERS, INCLUDING OSTEOPOROSIS

1. INTRODUCTION

The present invention relates to methods and compositions for the amelioration of symptoms caused by bone resorption disorders, including but not limited to osteoporosis, arthritides and periodontal disease, and damage caused by macrophage-mediated inflammatory processes.

In one embodiment, the methods and compositions of the invention include methods and compositions for the specific inhibition of cathepsin K activity. In an additional embodiment, the methods and compositions of the invention Include methods and compositions for the specific inhibition of cathepsin K activity coupled with specific inhibition of at least a second activity involved in the bone resorption and/or macrophage-mediated inflammatory processes. In a particular embodiment, the methods and compositions of the invention include methods and compositions for the specific inhibition of cathepsin K and cathepsin S activity.

2. BACKGROUND

Bone remodeling is a dynamic process which does not cease when longitudinal growth ceases, but continues throughout an individual's lifetime. Remodeling is required to preserve the mechanical strength of bone and involves both bone resorption and deposition. In order to maintain a constant adult skeletal mass, the rates of bone resorption and formation must be equal. (For a review, see, e.g., Rasmussen, H. & Bordier, P., 1974, The Physiological and Cellular Basis of Metabolic Bone Disease, Williams & Wilkins Co., Baltimore).

Bone formation and resorption are mediated by the temporally and spatially related actions of specific bone cells. Among these bone cells are osteoblasts and osteoclasts (for a review, see Rodan, C. A., 1992, Bone 13:S3). Osteoblasts are involved in bone formation processes, including organic matrix synthesis and mineralization. Osteoclasts are polarized, multinucleate cells involved in bone resorption processes. Such processes include the creation of an acidic environment which leads to bone demineralization, and the synthesis and production of proteinases which degrade the bone's organic matrix, 95% of which is Type I collagen (Krane, S. M. & Simon, L., 1994, in Scientific American Medicine, Rubenstein, E. & Felderman, D. D., eds., Scientific American, Inc., New York, pp. 1–26).

Among the proteinases that may be involved in bone organic matrix degradation and/or bone resorption are interstitial collagenase, and a complex group of acidic cysteine protease cathepsins of the papain superfamily (Kirschke, H. & Barrett, A. J., 1987, in Lysosomes: Their Role in Protein Breakdown, Glaumann, H. & Ballard, F. J., eds., Academic Press, London, pp. 193–238; Kirschke, H. et al., 1986, Biochem. J. 264:467–473) including cathepsin B (Ferrara et al., 1990, FEBS Lett. 273:195–199; Chan et al., 1986, Proc. Natl. Acad. Sci. U.S.A. 83:7721–7725), S (Shi, G.-P. et al., 1994, J. Biol. Chem. 269:11530–11536), L (Chauthan, S. S. et al., 1993, J. Biol. Chem. 268:1039–1045), O (Velasco, G. et al., 1994, J. Biol. Chem. 269:27136–27142) and a cathepsin which has been referred to alternatively as cathepsin O (unrelated to the above-mentioned O), OC2, O2, K or X (Tezuka, K. et al., 1994, J. Biol. Chem. 269:1106–1109; Li, Y. P. et al., 1994, Mol. Biol. Cell 5:335a; Shi, G.-P. et al., 1995, FEBS Lett. 357:129–134; Inaoka, T. et al., 1995, Biochem. Biophys. Res. Commun. 206:89–96; Bromme, D. & Okamoto, K., 1995, Biol. Chem. Hoppe-Seyler 376:379–386), and will be referred to herein as cathepsin K. Cathepsin K is expressed at high levels in osteoclast cells and in activated macrophages, but not in peripheral monocytes, despite the fact that osteoclasts and monocytes are derived from a common progenitor. Further, a number of cathepsin B-like and cathepsin-L-like activities have been reported (Page et al., 1992, Biochim. Biophys. Acta 1116:57–66) from osteoclastomas.

The identification of which of the cathepsins may be involved in bone resorption has been problematic, given, for example, the that osteoclasts are rare cells and no acceptable osteoclast cell line has been established (Drake, F. H. et al., 1996, J. Biol. Chem. 271:12511–12516). Nonetheless, there is evidence for cysteine proteases in bone resorption. For example, Delaisse et al. reported that cysteine protease inhibitors reduced bone resorption in a mouse bone organ culture system (Delaisse, J.-M. et al., 1980, Biochem. J. 192:365–368) and in calcium-deficient rats (Delaisse, J.-M. et al., 1984, Biochem. Biophys. Res. Commun. 125:441–447), and classified the enzyme responsible as cathepsin B. In contrast, however, Drake et al. reports that cathepsins B, H and L are either expressed at very low levels or are absent in osteoclasts, and speculates that cathepsin K, which, it is reported, is selectively and highly expressed in osteoclasts, is the important cathepsin in bone resorption (Drake, F. H. et al., 1996, J. Biol. Chem. 271:12511–12516). Thus, while one or more of the cathepsins may be involved in bone resorption and bone resorption disorders such as those discussed below, conflicting data exist relating to the relative importance of the individual cathepsins.

Any interference with the normal remodeling process can produce skeletal disease, with the most common skeletal disorders involving those associated with a decreased absolute skeletal mass, indicating that the rate of bone resorption exceeds the rate of bone formation. The most common of such disorders is osteoporosis. Other bone loss disorders include, for example, periodontal disease and certain arthritides such as osteoarthritis.

Osteoporosis comprises several different bone resorption disorders associated with a decreased bone mass in the absence of a mineralization defect, and is characterized by a decreased skeletal mass, declining density of bone, loss of trabeculations and a thinning of the cortices (see, e.g., Avioli, L. V. et al., 1990, in Metabolic Bone Disease and Clinical Related Disorders, Avioli, L. V. & Krane, eds., Saunders Co., Philadelphia, p. 397; Melton, L. J. & Riggs, B. L., 1989, in Clinical Disorders of Bone and Mineral Metabolism, Kleerekoper, M. & Krane, S. M., eds., Mary Ann Liebert, New York, p. 145, and Riggs, B. L. & Melton, L. J. III, 1986, N. Engl. J. Med. 314:1676).

The most common forms of osteoporosis, referred to collectively as involutional osteoporosis, accompany aging and occur particularly in women after menopause. In fact, osteoporosis is the most significant underlying cause of skeletal fractures in late middle age and elderly women. Estrogen deficiency has been strongly implicated as a factor in postmenopausal osteoporosis (Horowitz, M. C., 1993, Science 260:626).

As opposed to osteoporosis, osteosclerotic disorders involve an abnormal thickening or hardening of bone tissue. Among such disorders is pycnodysostosis (PYCNO) a rare, autosomal recessive trait characterized by osteosclerosis, short stature, acro-osteolysis of distal phalanges, bone fragility, clavicular dysplasia and skull deformities with delayed suture closure (Maroteaux, P. & Lamy, M., 1962, Presse Med. 70:999; Andren, L. et al., 1962, Acta. Chir. Scand. 124:496). To date, no causative agent of the PYCNO disorder has been identified.

PYCNO is classified as an abnormality of primary spongiosa resorption (Greenspan, A., 1991, Skeletal Radiol. 20:561). Histologically, osteoclast numbers, ruffled borders, and clear zones are normal, but the region of demineralized bone surrounding individual osteoclasts is increased (Everts, V. et al., 1985, Calcif. Tissue Int. 37:25), and ultrastructural examination of osteoclasts reveal occasional large abnormal cytoplasmic vacuoles containing bone collagen fibrils. Such findings suggest that PYCNO osteoclasts may be impaired in demineralizing bone and/or in degrading the organic matrix.

The gene responsible for PYCNO has not, to date, been identified. A genome-wide search for the PYCNO locus involving a large, consanguineous Israeli Arab family with 16 affected relatives identified a genomic region that was homozygous-by-descent for all affected individuals (Gelb, B. D. et al., 1995, Nature Genet. 10:235). This region was localized to a pericentric portion of chromosome 1 with a lod score of 11.72 at D1S498 and ancestral recombination events localized the PYCNO region to 4 cM from D1S442 to D1S305. Independent linkage analysis of a large Mexican family confirmed linkage to the chromosome 1 pericentric region and excluded the macrophage colony stimulating factor, CSF1, which is defective in the op/op mouse model of osteoporosis (Polymeropoulos, M. H. et al., 1995, Nature Genet. 10:238).

No adequate treatments exist for bone disorders such as those described herein. With respect to osteoporosis, current treatment can, at best, attempt to prevent further bone loss and, if possible, restore bone mass to some extent. Osteoporosis therapies can include estrogen (Albright, F. et al., 1941, JAMA 116:2465), calcium supplements (Prince, R. L. et al., 1991, N. Engl. J. Med. 325:1189) and vitamin D supplements (Chapuy, M. C. et al., 1992, N. Engl. J. Med. 327:1637). Further treatments can include sodium fluoride (Riggs, B. L. et al., 1992, N. Engl. J. Med. 327:620), androgen (Nagent de Deuxchaisnes, C., 1983, in Osteoporosis, a Multi-Disciplinary Problem, Royal Society of Medicine International Congress and Symposium Series No. 55, Academic Press, London, p. 291), calcitonin (Christiansen, C., 1992, Bone 13 (Suppl. 1):S35) or biphosphonate (Storm, T. et al., 1990, N. Engl. J. Med. 322:1265; Watts, N. B. et al;., 1990, N. Engl. J. Med. 323:73). Further, experimental therapies such as synthetic parathyroid hormone analogue (Hock, J. M. et al., 1990, Endocrinology 127:1804) or thiazide diuretics (Cauley, J. A. et al., 1993, Ann. Intern. Med. 118:666) have also been attempted.

In summary, no agent responsible, in vivo, for bone matrix degradation has, to date, been identified. A great need exists for the definitive identification of targets for the treatment of bone disorders, including bone resorption disorders, such as osteoporosis and osteosclerotic disorders.

3. SUMMARY OF THE INVENTION

The present invention relates, first, to methods and compositions for the amelioration of symptoms caused by bone resorption disorders, including but not limited to osteoporosis, arthritides such as osteoarthritis, and periodontal disease, and damage caused by macrophage-mediated inflammatory processes.

The present invention is based, in part, on the Applicants' definitive demonstration that cathepsin K is essential to bone resorption. This discovery represents the first demonstration of an agent which acts in vivo to degrade bone matrix. The present invention is further based on the surprising discovery that the bone resorptive process may require not only cathepsin K, but may also require the presence one or more additional proteases and/or other components of the bone matrix hydrolyzing system.

In one embodiment, the methods of the invention comprise methods for ameliorating symptoms of bone resorption disorders and/or macrophage-mediated inflammatory damage via methods for the specific inhibition of cathepsin K activity.

In an additional embodiment, the methods of the invention include methods for the specific inhibition of at least a second activity involved in bone resorption and/or macrophage-mediated inflammatory damage processes. Such an activity or activities can include, but is (are) not limited to, activities that control cathepsin K expression, activation, biosynthesis, processing, catalytic function, stability, intracellular transport, osteoclast-specific expression or enhanced expression, osteoclastic secretion, macrophage expression or enhanced expression and/or macrophage-mediated secretion. Such an activity or activities can also include, for example, activities required for coordinated matrix degradation, including, but not limited to, activities involving another cathepsin, for example, cathepsin S, L, B, D and/or O. Further, such activities can include, but are not limited to, activities involving availability or prior processing of a cathepsin substrate for cathepsin hydrolysis; generation of active osteoclasts from their monocyte/macrophage progenitors; and function of osteoclasts in creating the acidic, sealed microenvironment of the subosteoclastic space.

In a further embodiment, the methods of the invention comprise methods for the specific inhibition of cathepsin K activity coupled with specific inhibition of at least a second activity, as described above, involved in bone resorption and/or macrophage-mediated inflammatory damage processes. For example, in a particular embodiment, the methods of the invention include methods for the specific inhibition of cathepsin K and cathepsin S activities.

It is also contemplated that polymorphisms and/or mutations within the cathepsin K gene can affect bone density in individuals carrying alleles containing such polymorphisms and/or mutations. As such, it is a further object of the invention to provide methods for the detection of bone-density-affecting polymorphisms within the cathepsin K gene.

The compositions of the invention include, in one embodiment, compositions, including pharmaceutical compositions, for the specific inhibition of cathepsin K activity. Such compositions of the present invention can include, but are not limited to, inhibitors of cathepsin K gene activity, such as, for example, cathepsin K antisense, triple helix and/or ribozyme molecules, and inhibitors of cathepsin K enzymatic activity.

Cathepsin K specific inhibitors can also include, but are not limited to, specific inhibitors belonging to the following, preferably peptidyl, classes of compounds: fluoromethyl ketones, vinyl sulfones, peptide aldehydes, nitriles, α-ketocarbonyl compounds, including, for example, α-diketones, α-keto esters, α-ketoamides, and α-ketoacids, halomethyl ketones, diazomethyl ketones, (acyloxy)-methyl ketones, ketomethylsulfonium salts and epoxysuccinyl compounds.

In a further embodiment, the compositions of the invention include compositions, including pharmaceutical compositions, for the specific inhibition of cathepsin K activity and at least a second activity, as described above, involved in bone resorption and/or macrophage-mediated inflammatory damage processes. For example, in a particular embodiment, the compositions include compositions, including pharmaceutical compositions, for the specific inhibition of cathepsin K and cathepsin S activities.

In instances in which the additional activity or activities is (are) additional cathepsin activities, the additional cathepsin specific inhibitors can also include, but are not limited to, specific inhibitors belonging to the following, preferably peptidyl, classes of compounds: fluoromethyl ketones, vinyl sulfones, peptide aldehydes, nitriles, α-ketocarbonyl compounds, including, for example, α-diketones, α-keto esters, α-ketoamides, and α-ketoacids, halomethyl ketones, diazomethyl ketones, (acyloxy)-methyl ketones, ketomethylsulfonium salts and epoxysuccinyl compounds.

The present invention additionally relates to methods and compositions for the amelioration of symptoms caused by osteosclerotic bone disorders, including but not limited to pycnodysostosis (PYCNO).

Further, the present invention relates to isolated osteoclast cells and cell lines deficient for cathepsin K and/or other cathepsin activities. Still further, the present invention relates to genetically engineered nonhuman animals deficient for cathepsin K and other cathepsin activities.

The Example presented in Section 6 demonstrates that the osteosclerotic bone disorder PYCNO is caused by a deficiency of cathepsin K activity. By elucidating the cause of the natural PYCNO disorder, the present invention definitively identifies for the first time, an agent, cathepsin K, which degrades bone matrix in vivo and which is essential to bone resorption.

The Example presented in Section 7, below, indicates that a mutation or polymorphism within at least one other (i.e., second) gene locus appears to predispose individuals to PYCNO, indicating that the disease requires the presence of at least two mutations, one present in the cathepsin K gene and at least one additional mutation present in a second gene involved in the bone resorption process. The example presented in Section 8 describes the genomic structure of the human cathepsin K gene.

4. BRIEF DESCRIPTION OF THE FIGURES

FIG. 1. Pycnodysostosis (PYCNO) critical region at chromosome 1q21. The microsatellite markers flanking and within the PYCNO critical region are shown in the order established previously (Gelb, B. D. et al., 1996, Hum. Genet. 98:141–144). Two overlapping CEPH megaYAC clones which were positive for the cathepsin S and K STSs are indicated and anchored by D1S498.

Figure 2:
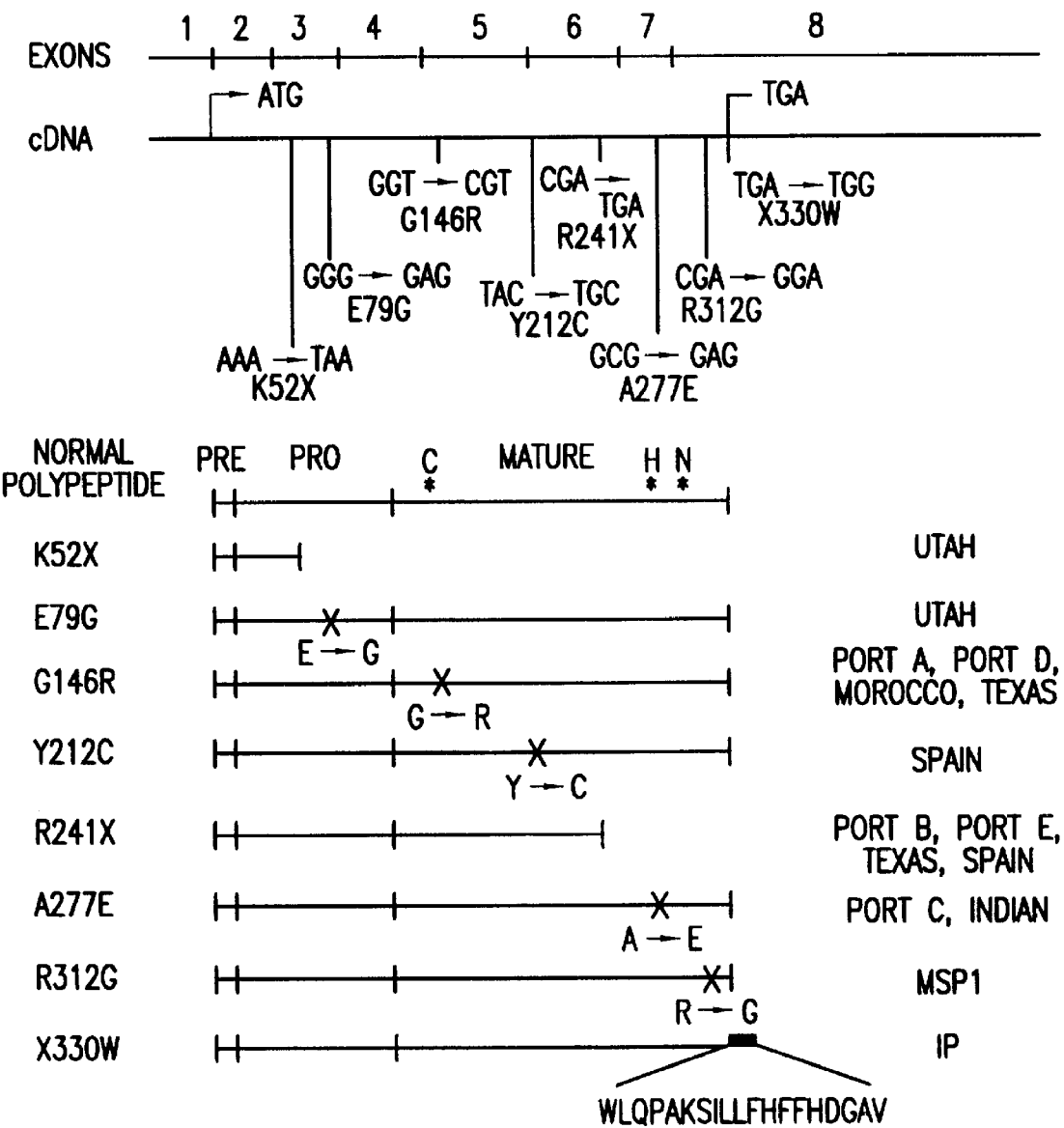

FIG. 2. Cathepsin K cDNA and polypeptide with PYCNO mutations. The top line represents the cathepsin K exon structure; the second line represents the cDNA with initiation (ATG) and stop (TGA) codons as indicated. The locations of the eight mutations are indicated below the cDNA, showing both the affected codon and the predicted amino acid alteration. The normal cathepsin K polypeptide is shown with the pre-, pro-, and mature peptides. The three residues (C, H, N) in the active site conserved among all cysteine protease cathepsins in the papain superfamily are indicated. The K52X and R241X mutations are nonsense mutations resulting in truncated proteins, the E79G, G146R, Y212C, A277E and R312G mutations are missense mutations and the X330W mutation is shown with the predicted elongation of the mature peptide by 19 residues. At the right are listed the families in which the respective mutations were found. (Port.=Portugal; MSP=Mount Sinai PYCNO patient; IP=Israeli PYCNO patient).

Figure 3A:
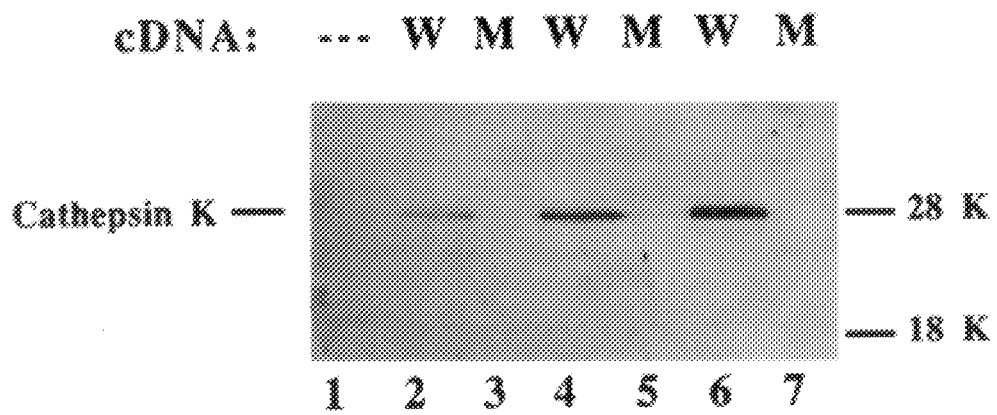
Figure 3B:
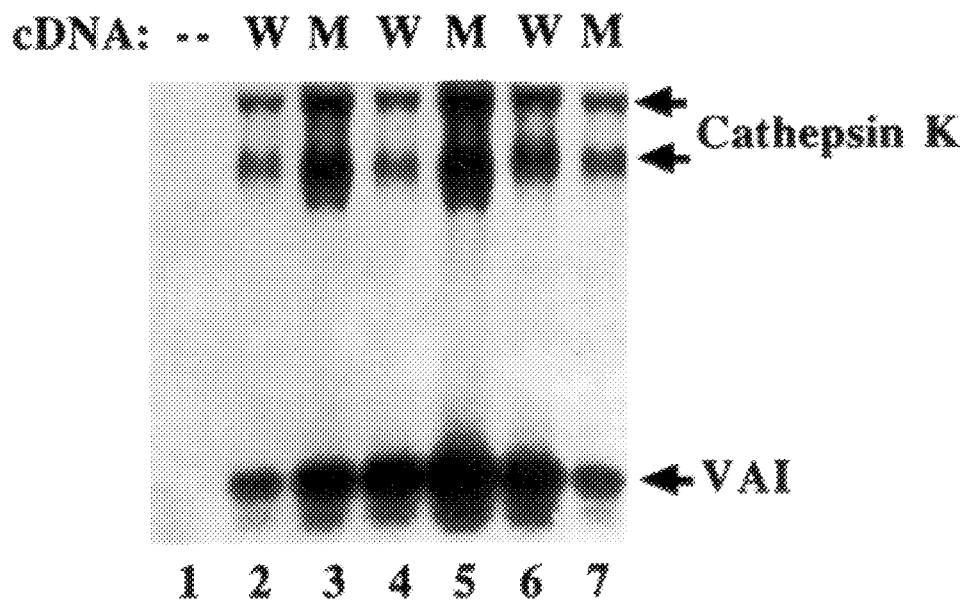

FIG. 3A–3B. Transient expression of the X330W mutation in cathepsin K. (A) Wild type and X330W cDNAs were subcloned into the pcDNA-1 expression vector (Invitrogen) (Shi, G.-P. et al., 1995, FEBS Lett. 357:129; Bromme, D. & Okamoto, K., 1995, Biol. Chem. Hoppe-Seyler 376:37; Tezuka, K., et al., 1994, J. Biol. Chem. 269:1106; Inaoka, T., et al., 1995, Biochem. BioPhys. Res. Commun. 206:89) and confirmed by PCR, restriction enzyme digestions and dideoxy chain termination sequencing. Both constructs were transfected into 293 cells using LipofectAMINE (GibcoBRL) along with 3 μg pAdVAmtage™ (Promega) which contains the adenovirus virus-associated I RNA (VAI) to enhance translation (Kaufman, R. J. & Murtha, P., 1987, Mol. Cell. Biol. 7:1568). Cells were harvested after 48 h post-transfection and assayed by immunoblotting. Blots were developed with monospecific polyclonal anti-human cathepsin K antibodies raised by injection of cathepsin K-maltose binding protein fusion protein into rabbits and purified by elution from immobilized antigen as described (Munger, J. S. et al., 1995, Biochem. J., 311:299). Lane 1 shows results with nontransfected cells. Lanes 2–3, 4–5, and 6–7 show results with cells transfected with 3, 10 or 15 μg, respectively, of wild-type (W) or mutant (M) cDNA. (B) Total RNA was isolated from both transfected and nontransfected 293 cells and 40 μg of total RNA was separated on a 2.4% agarose gel. Northern blot was hybridized with [$^{32}$P]-labeled probes of both cathepsin K and VAI. Transcripts of both cathepsin K and VAI are indicated. Lanes 1 to 7 have the same order as in (A).

Figure 4:
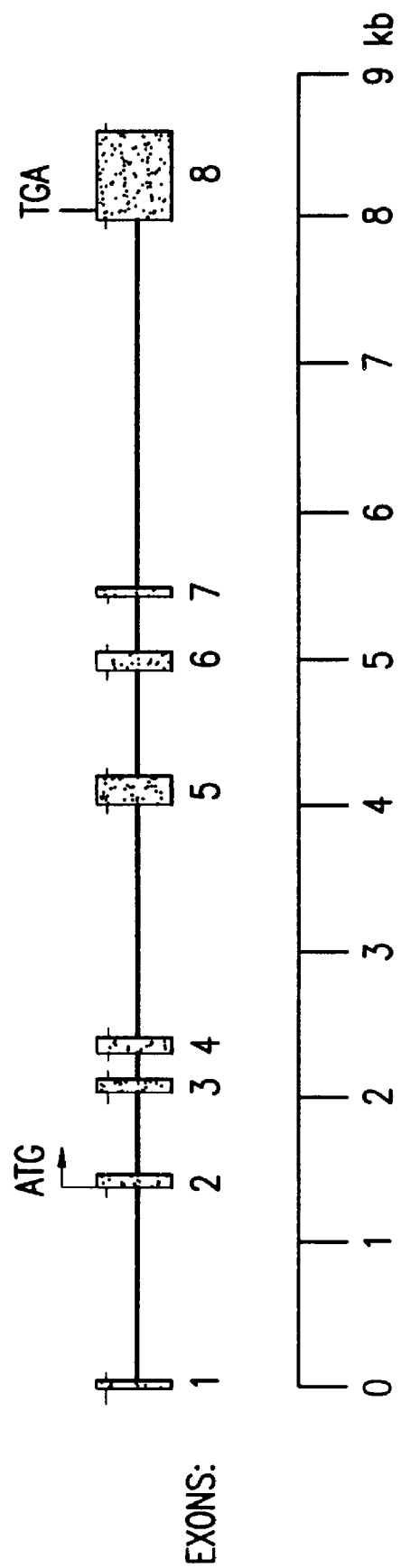

FIG. 4. Genomic organization of the human cathepsin K gene. The eight exons are shown as black boxes with the translation initiation ATG and TGA stop codons indicated. The seven introns are indicated by the thick black lines. The cumulative size of the cathepsin K genomic sequence is shown on the scale below.

Figure 5:
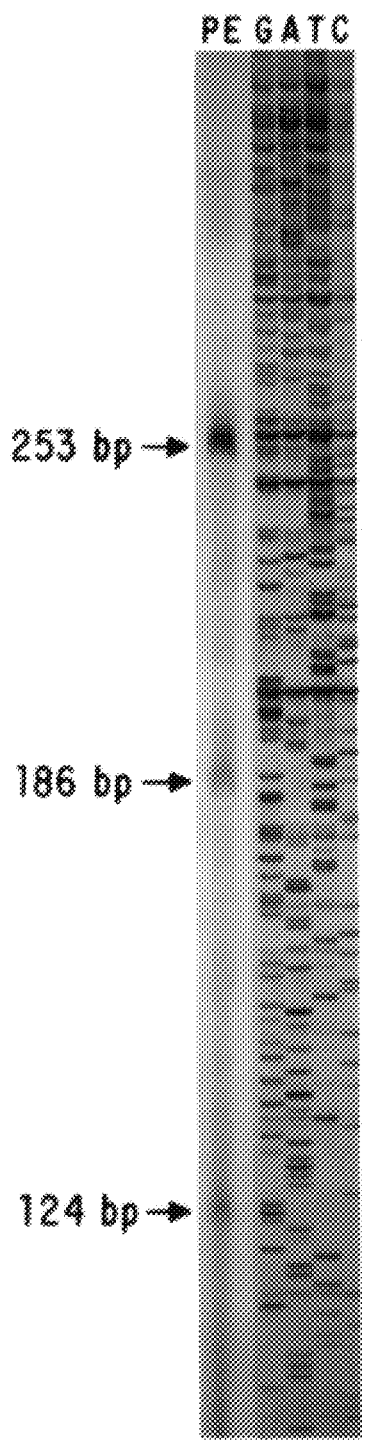

FIG. 5. Identification of the human cathepsin K transcription initiation sites by primer extension. Fifty micrograms of human brain total RNA was used for the primer extension (PE) reaction with an antisense primer from nucleotides +84 to +60. The primer extension products were determined to be 124, 186, and 253 bp in length by denaturing polyacrylamide gel electrophoresis using the adjacent DNA sequencing reaction (GATC) as a size marker. This corresponded to expected 5' UTRs of 40, 102, and 169 nt, respectively.

FIG. 6. Sequence of human cathepsin K exon 1 (SEQ ID NO: 1)and upstream flanking region with comparison to the published 5' untranslated regions from cathepsin K cDNA clones (SEQ NOS: 2–5(capitalized) and upstream flanking (lowercase) sequence was derived from PAC 74e16. The three transcription initiation sites from primer extension analysis are indicated in bold type. The 5' untranslated regions from four different cathepsin k cDNA clones are aligned to exon 1 with identical bases indicated. The sense primer sequence, CTSK43, used for PCR amplification from first strand cDNA (see Section 8, below) is underlined. Two putative AP1 binding sites in the upstream flanking region are also underlined.

5. DETAILED DESCRIPTION OF THE INVENTION

5.1. COMPOUNDS FOR THE AMELIORATION OF SYMPTOMS ASSOCIATED WITH BONE RESORPTION DISORDERS

Described herein are compositions, including pharmaceutical compositions, which can be utilized for the amelioration of symptoms associated with bone resorption disorders, including, but not limited to, osteoporosis, arthritides such as osteoarthritis, and periodontal disease, and damage caused by macrophage-mediated inflammatory processes. Such compositions can include, but are not limited to, small peptides, small organic molecules, antisense, ribozyme and triple helix molecules.

Among the compositions of the invention are compositions, including pharmaceutical compositions, which represent specific inhibitors of cathepsin K activity. Pharmaceutical compositions of the invention are described in Section 5.2.1, below.

The term "specific", as used herein, refers to a composition that reduces the level of cathepsin K enzymatic activity to a greater extent than it reduces the enzymatic activity levels of other cysteine proteases, serine proteases, metalloproteases and aspartyl proteases. Preferably, an inhibitor of this class reduces the level of cathepsin K activity while not appreciably affecting the enzymatic activity of other such proteases. While not wishing to be bound by a particular mechanism, the inhibitors can act, for example, by lowering the level of cathepsin K gene expression or may act directly on the cathepsin K enzyme to inhibit or suppress enzymatic activity.

In instances wherein the inhibitor of this class is to be used in conjunction with the inhibition of at least a second activity involved in bone resorption and/or macrophage-mediated inflammatory damage processes, such an inhibitor is still considered a "specific" inhibitor when it reduces the level of an additional activity or activities to a greater extent than it reduces other activities, such as, for example, other cysteine protease activities. For example, in a particular embodiment wherein cathepsin K and cathepsin S activities are to be inhibited, a specific inhibitor of this class can refer to a composition which inhibits both cathepsin K and cathepsin S activities to a greater extent than it reduces the activities of other cysteine proteases.

Among the cathepsin K specific inhibitors are those molecules identified via the methods described, below, in Section 5.4. Additionally such inhibitors can include, for example, antisense, ribozyme and triple helix molecules, as described in Section 5.1.1, below.

Cathepsin K specific inhibitors can also include, but are not limited to, specific inhibitors belonging to the following, preferably peptidyl, classes of compounds: fluoromethyl ketones, vinyl sulfones, peptide aldehydes, nitriles, α-ketocarbonyl compounds, including, for example, α-diketones, α-keto esters, α-ketoamides, and α-ketoacids, halomethyl ketones, diazomethyl ketones, (acyloxy)-methyl ketones, ketomethylsulfonium salts and epoxysuccinyl compounds.

Cathepsin K specific inhibitors can further include, but are not limited to, cathepsin K proenzyme peptides. Such pro enzyme peptides comprise the "propart" region of cathepsin K protein independent of the mature cathepsin K protein sequence. The cathepsin K propart generally refers to the 98 amino acid sequence at the N-terminus of the cathepsin K proenzyme which remains after cleavage of the "pre" leader sequence. (See, e.g., Shi, G.-P. et al., 1995, FEBS Lett. 357:129–134, which is incorporated herein by reference in its entirety.)

The compositions of the invention can further include specific inhibitors of at least a second activity involved in bone resorption and macrophage-mediated inflammatory damage processes. The compounds in this class of inhibitors include, but are not limited to, specific inhibitors of a gene product involved in cathepsin K expression, biosynthesis, processing, activation, catalytic function, intracellular transport, stability, osteoclast-specific expression or enhanced expression, osteoclastic secretion, macrophage expression or enhanced expression and/or macrophage secretion.

Further, the compounds in this class include, but are not limited to, specific inhibitors of a gene product involved in the availability or prior processing of the cathepsin K substrate(s) for hydrolysis by cathepsin K.

Still further, the compounds in this class include, but are not limited to, inhibitors of: another cathepsin, such as, for example, cathepsin S, L, B, D and/or O; a gene product involved in the expression, enzymatic activity and/or substrate availability of such an additional cathepsin; the generation of active osteoclasts from their monocyte/macrophage progenitors; and/or a gene product involved in the function of osteoclasts such as, for example, in creating the acidic, sealed microenvironment of the subosteoclastic space.

The term "specific", as used herein, refers to a composition that reduces (that is, inhibits or suppresses) the activity level or levels of interest, to a greater extent than it reduces the remainder of the activities listed above. For example, if the composition is an inhibitor of a second activity relating to cathepsin K activity, then the inhibitor is a specific one if its effect is to reduce the level of cathepsin K activity to a greater extent than it reduces the activity of other cysteine proteases, including serine proteases, aspartyl proteases, etc.

When an inhibitor of this class is to be utilized coupled with an inhibitor of cathepsin K activity, it is to still be considered a specific inhibitor if it inhibits both the second activity of interest (cathepsin S activity, for example) as well as inhibiting cathepsin K activity to a greater extent than it reduces the activity of the remainder of the activities listed above. Further, an inhibitor of this class is still considered a specific inhibitor if the composition inhibits both cathepsin K activity and the second activity of interest (such as, for example, cathepsin S activity).

5.1.1. Antisense, Ribozyme and Triple Helix Inhibitors

Among the inhibitors of the invention are nucleic acid antisense, ribozyme and/or triple helix molecules which act to inhibit expression of genes involved in one or more of the activities relating to bone resorption and/or macrophage-mediated inflammatory damage processes. Such inhibitors can be utilized in methods for the amelioration of symptoms caused by bone resorption disorders and/or macrophage-mediated inflammatory damage. For purposes of clarity, antisense, triple helix and ribozyme inhibitors of cathepsin K gene expression will frequently be used here as an example and not by way of limitation.

Antisense or ribozyme approaches can be utilized to inhibit or prevent translation of mRNA transcripts; triple helix approaches to inhibit transcription of the gene of interest itself.

Antisense approaches involve the design of oligonucleotides (either DNA or RNA) that are complementary to mRNA, cathepsin K mRNA, for example. The antisense oligonucleotides bind to the complementary mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. See generally, Wagner, R., 1994, Nature 372:333–335. Thus, taking cathepsin K as an example, oligonucleotides complementary to the 5'-non-translated, non-coding region, as shown in FIG. 6, and/or the 3'-non translated, non-coding region (see, e.g., Tezuka, K. et al., 1994, J. Biol. Chem. 269:1106–1109, which is incorporated herein by reference in its entirety) the cathepsin K gene could be used in an antisense approach to inhibit translation of endogenous cathepsin K mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of cathepsin K mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual α-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the cathepsin K coding region sequence could be used, those complementary to the transcribed untranslated region are most preferred.

The antisense molecules should be delivered to cells which express cathepsin K in vivo, e.g., osteoclast and/or macrophage cells. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transect target cells in the patient will result in the transcription of sufficient amounts of single stranded RNAs that will form complementary base pairs with the endogenous cathepsin K transcripts and thereby prevent translation of the cathepsin K mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systemically).

Ribozyme molecules designed to catalytically cleave cathepsin K mRNA transcripts can also be used to prevent translation of cathepsin K mRNA and expression of cathepsin K enzyme. (See, e.g., PCT International Publication WO90/11364, published Oct. 4, 1990; Sarver et al., 1990, Science 247:1222–1225). While ribozymes that cleave mRNA at site specific recognition sequences can be used to destroy cathepsin K mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are many potential hammerhead ribozyme cleavage sites within the nucleotide sequence of human cathepsin K, the sequence of which is well known to those of skill in the art. Preferably the ribozyme is engineered so that the cleavage recognition site is located near the 5' end of the cathepsin K mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429– 433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in cathepsin K.

As in the antisense approach, the ribozymes can be composed of modified oligonucleotides (e.g. for improved stability, targeting, etc.) and should be delivered to cells which express the cathepsin K gene in vivo, e., osteoclasts and/or macrophage cells. A preferred method of delivery involves using a DNA construct "encoding" the ribozyme under the control of a strong constitutive pol III or pol II promoter, so that transfected cells will produce sufficient quantities of the ribozyme to destroy endogenous cathepsin K messages and inhibit translation. Because ribozymes, unlike antisense molecules, are catalytic, a lower intracellular concentration is required for efficiency.

Alternatively, endogenous cathepsin K gene expression can be reduced by targeting deoxyribonucleotide sequences complementary to the regulatory region of the cathepsin K gene (i.e., the cathepsin K promoter and/or enhancers) to form triple helical structures that prevent transcription of the cathepsin K gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15). Such cathepsin K regulatory sequences can readily be obtained by one of ordinary skill in the art by utilizing standard molecular biological techniques coupled with the cathepsin K gene 5' untranslated nucleotide sequence depicted herein in FIG. 6.

5.2. METHODS FOR AMELIORATION OF SYMPTOMS ASSOCIATED WITH BONE RESORPTION DISORDERS

This Section describes methods for the amelioration of bone resorption disorders, including, but not limited to osteoporosis, arthritides such as osteoarthritis, and periodontal disease, and damage caused by macrophage-mediated inflammatory processes. Macrophage-mediated inflammatory damage can include, but it is not limited to, macrophage-mediated periodontal disease damage and osteoarthritic damage. Such macrophage-mediated inflammatory damage can further include damage in addition to specifically bone-related damage, such as, for example, lung injury associated with emphysema, and injury associated with an accumulation of macrophages at the site of atherosclerotic plaques. In general, the methods of the invention can be utilized for ameliorating abnormal or excessive damage which occurs due to macrophage accumulation at sites of injury.

The methods of the invention further include methods for the specific inhibition of at least a second activity involved in bone resorption and/or macrophage-mediated inflammatory damage processes. Such an activity or activities can include, but is (are) not limited to, activities that control cathepsin K expression, activation, biosynthesis, processing, catalytic function, stability, intracellular transport, osteoclast-specific expression or enhanced expression, osteoclastic secretion, macrophage expression or enhanced expression and/or macrophage-mediated secretion. Such an activity or activities can also include, for example, activities required for coordinated matrix degradation, including, but not limited to, activities involving another cathepsin, for example, cathepsin S, L, B, D and/or O. Further, such activities can include, but are not limited to, activities involving availability or prior processing of a cathepsin substrate for cathepsin hydrolysis; generation of active osteoclasts from their monocyte/macrophage progenitors; and function of osteoclasts in creating the acidic, sealed microenvironment of the subosteoclastic space.

In a further embodiment, the methods of the invention include methods for the specific inhibition of cathepsin K activity coupled with specific inhibition of at least a second activity, as described above, involved in bone resorption and/or macrophage-mediated inflammatory damage processes. For example, in a particular embodiment, the methods of the invention include methods for the specific inhibition of cathepsin K and cathepsin S activities.

A method for ameliorating symptoms of a bone resorption disorder and/or symptoms of macrophage-mediated inflammatory damage, can, for example, comprise: contacting a cell with a cathepsin K inhibitor for a time sufficient to inhibit cathepsin K activity so that symptoms of the disorder or damage are ameliorated. The cathepsin K inhibitor can include, but is not limited to, the cathepsin K inhibitor compositions, including pharmaceutical compositions, described in Section 5.1, above.

A method for ameliorating symptoms of a bone resorption disorder and/or symptoms of macrophage-mediated inflammatory damage, can also, for example, comprise: contacting a cell with an inhibitor of at least a second activity involved in a bone resorption process and/or a macrophage-mediated inflammatory damage process, for a time sufficient to inhibit the activity so that symptoms of the bone resorption disorder are ameliorated. The inhibitor can include, but is not limited to the inhibitor compositions, including pharmaceutical compositions, described in Section 5.1, above.

A method for ameliorating symptoms of a bone resorption disorder and/or symptoms of macrophage-mediated inflammatory damage, can, for example, still further, comprise: contacting a cell with a cathepsin K inhibitor and an inhibitor of at least a second activity involved in a bone resorption process and/or a macrophage-mediated inflammatory damage process, for a time sufficient to inhibit the activity so that symptoms of the bone resorption disorder are ameliorated. In a particular embodiment of such a method, the second activity is a cathepsin S activity.

It is envisioned that, in certain instances, a single composition or pharmaceutical composition will represent both the cathepsin K inhibitor and the inhibitor of the at least second activity. In a particular embodiment, such an inhibitor inhibits both cathepsin K and cathepsin S activities.

It should be noted that in addition to such a second activity, the methods of the invention also include administration of inhibitors of additional (i.e., third, fourth, etc.) activities in combination for the amelioration of said symptoms.

When a combination of inhibitors is being utilized as part of such methods of the invention, it is to be understood that the inhibitors can be administered simultaneously or sequentially. If administered simultaneously, the inhibitors can be administered in any order most beneficial to ameliorating symptoms of the disorder or damage. One of reasonable skill in the art will, depending on the particular inhibitors and disorder or damage being treated, readily appreciate the most advantageous administration strategy to follow.

5.2.1. PHARMACEUTICAL PREPARATIONS AND METHODS OF ADMINISTRATION

Compositions to be administered as part of methods for ameliorating symptoms of bone resorption disorders and/or macrophage-mediated inflammatory damage are to be administered to a patient at therapeutically effective doses to treat or ameliorate symptoms of such disorders. A therapeutically effective dose refers to that amount of the compound sufficient to result in amelioration of symptoms of bone resorption disorders and/or macrophage-mediated inflammatory damage.

The inhibitory compositions of the invention can be administered as pharmaceutical compositions. Such pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or topical, oral, buccal, parenteral or rectal administration.

The inhibiting compositions of the invention can further be administered in conjunction with standard dental techniques for the amelioration and/or prevention of macrophage-mediated inflammatory damage associated with, for example, periodontal disease. The compositions can be administered in any form convenient for application to the gum and sub-gum area, in the form of a toothpaste in any form (gel, powder, foam) or a mouthwash. Further, the compositions can be administered during periodontal surgical procedures, deep cleanings and the like.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.3. METHODS FOR AMELIORATION OF OSTEOSCLEROTIC BONE DISORDER-ASSOCIATED SYMPTOMS

Described herein are methods for the amelioration of symptoms caused by osteosclerotic bone disorders, including but not limited to PYCNO. In one embodiment of such methods, the methods serve to increase the level of cathepsin K gene and/or enzyme activity. In an additional embodiment, such methods serve to increase both cathepsin K gene and/or enzyme activity as well as increasing the level of at least a second gene and/or enzyme activity involved in causing osteosclerotic bone disorders. In a particular embodiment, such methods increase the level of cathepsin K and cathepsin S gene and/or enzyme activity.

As an example for purposes of clarity and not by way of limitation, the description herein will frequently use as an example an increase in cathepsin K gene and/or enzyme activity.

With respect to an increase in cathepsin K enzyme activity, enzyme replacement therapy can, for example, be utilized. By following standard techniques, levels of cathepsin K enzyme can be augmented to a concentration which ameliorates symptoms of osteosclerotic bone disorders, including PYCNO. Enzyme replacement, here, involves the administration of exogenous enzyme, for example cathepsin K enzyme, into a patient at a concentration sufficient to ameliorate osteosclerotic disorder symptoms. Administration can, for example, be intravenous. Alternatively, enzyme can be administered directly to a site or sites of desired action, in this case to bone tissue, especially to the site of bone resorption, including the site of bone remodeling and matrix degradation.

The cathepsin K enzyme utilized will include, preferably, the proenzyme form of cathepsin K. In instances in which the osteosclerotic disorder involves an inability to successfully process the proenzyme into the active form, the active form of cathepsin K is administered. In these instances, site-specific, rather than systemic administration is preferred. Dosage ranges necessary for amelioration of osteosclerotic disorders can readily be determined by one of skill in the art following, for example, techniques such as those described, above, in Section 5.2.1. Such dosage ranges can include, for example, an administration of enzyme at a concentration ranging from about 0.1 $\mu$g/kg to about 10 mg/kg, preferably from about 0.1 mg/kg to about 2 mg/kg.

With respect to an increase in the level of normal cathepsin K gene expression, cathepsin K nucleic acid sequences can be utilized for the amelioration of symptoms caused by osteosclerotic bone disorders. Where the cause of such a disorder is a defective cathepsin K gene, treatment can be administered, for example, in the form of gene replacement therapy. Specifically, one or more copies of a normal cathepsin K gene or a portion of the cathepsin K gene that directs the production of a cathepsin K gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Appropriate cells include cell types in which cathepsin K gene expression is normally observed, especially osteoclast cells. Administration techniques can involve, for example, direct administration of cathepsin K gene sequences to the site of the cells in which the cathepsin K gene sequences are to be expressed, such as, for example, to the site of osteoclasts within bone tissue, and, especially, the site of bone remodeling, including the site of bone resorption.

Alternatively, targeted homologous recombination can be utilized to correct the defective endogenous cathepsin K gene in the appropriate tissue; e.g., osteoclast cells or osteoclast precursor cells. In non-human animals, targeted homologous recombination can be used to correct the defect in ES cells in order to generate offspring with a corrected cathepsin K and, therefore, a corrected trait.

Additional methods which may be utilized to increase the overall level of cathepsin K gene expression and/or cathepsin K activity include the introduction of appropriate cathepsin K-expressing cells, preferably autologous cells, into a patient at positions and in numbers which are sufficient to ameliorate the symptoms of osteosclerotic bone disorders, including PYCNO. Such cells may be either recombinant or non-recombinant.

Among the cells which can be administered to increase the overall level of cathepsin K gene expression in a patient are normal cells, preferably osteoclast cells which express the cathepsin K gene, and/or osteoclast precursor cells which give rise to cathepsin K-expressing osteoclast cells. Such cell-based gene therapy techniques are well known to those skilled in the art, see, e.g., Anderson, et al., U.S. Pat. No. 5,399,349; Mulligan & Wilson, U.S. Pat. No. 5,460,959.

In a particular embodiment, an autologous bone marrow procedure can be utilized to isolate osteoclast precursor cells from a patient suffering from an osteosclerotic bone disorder or from an individual predisposed to such a disorder. The isolated cells can be modified so as to contain a normal cathepsin K gene and reintroduced into the recipient so that osteoclast cells which express normal cathepsin K gene activity are produced in the patient, thereby ameliorating symptoms of the osteosclerotic disorder.

In another particular embodiment, the patient is deficient in both cathepsin K gene and/or enzyme activity as well as in a second gene whose absence is involved in osteosclerotic bone disorders. In such an embodiment, the isolated osteoclast precursor cells are modified so as to contain a normal cathepsin K gene and a normal second gene. The modified isolated precursor cells are reintroduced into the recipient so that osteoclast cells which express normal cathepsin K gene activity and normal second gene activity are produced in the patient, thereby ameliorating symptoms of the osteosclerotic disorder. In a particular example of such an embodiment, the second gene is a cathepsin S gene.

Because isolated bone marrow cells will contain osteoclast precursor cells, bone marrow can be obtained using standard techniques well known to those of skill in the art and modified, as described above, with no further cell separation or cell type purification.

In instances in which the cells utilized are to be autologous cells, the bone marrow is obtained form the patient to be treated. In instances in which the cells utilized are heterologous cells, the cells are chosen according to standard heterologous transplant criteria well known to those of skill in the art.

Alternatively, standard separation techniques can be used for the purification or partial purification of osteoclast precursor cells. Such separation techniques are generally based on the presence or absence of specific cell surface markers, preferably transmembrane markers, and the appropriate osteoclast precursor cell surface marker or combination of markers which are unique to the osteoclast precursor cells. Such a cell surface marker or combination of markers are well known to those of skill in the art.

Purification techniques can take advantage of such a cell surface marker or combination of markers by, for example, utilizing antibodies which bind the specific markers. These techniques can include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces or magnetic separations using antibody-coated magnetic beads.

A common technique for antibody based separation is the use of flow cytometry such as by a fluorescence activated cell sorter (FACS). Typically, separation by flow cytometry is performed as follows. The suspended mixture of cells is centrifuged and resuspended in media. Antibodies which are conjugated to fluorochrome are added to allow the binding of the antibodies to specific osteoclast precursor cell surface markers. The cell mixture is then washed by one or more centrifugation and resuspension steps. The mixture is run through a FACS which separates the cells based on different fluorescence characteristics. FACS systems are available in varying levels of performance and ability, including multicolor analysis. The osteoclast precursor cell can be identified by a characteristic profile of forward and side scatter which is influenced by size and granularity, as well as by expression of cell surface markers.

Other separation techniques besides flow cytometry can also provide fast separations. One such method is biotin-avidin based separation by affinity chromatography. Typically, such a technique is performed by incubating cells with biotin-coupled antibodies to specific markers, followed by passage through an avidin column. Biotin-antibody-cell complexes bind to the column via the biotin-avidin interaction, while other cells pass through the column. The specificity of the biotin-avidin system is well suited for rapid positive separation. Multiple passages can ensure separation of a sufficient level of the osteoclast precursor cell subpopulation of interest.

Upon isolation, and further separation if desired, if cell viability and recovery are sufficient, cells can be modified prior to introduction or reintroduction into the patient by, for example, transformation with gene sequences encoding a normal cathepsin K gene, and/or at least a second gene encoding a second gene product involved in bone resorption processes. Such modification is generally contemplated where autologous cells are concerned. For example, sequences can be introduced into the isolated autologous cells which encode a normal cathepsin K and normal cathepsin S gene products. Cell transformation and gene expression procedures are well known to those of skill in the art.

Cells, whether modified or not, can be cultured and expanded ex vivo prior to administration to a patient. Expansion can be accomplished via well known techniques utilizing physiological buffers or culture media in the presence of appropriate expansion factors such as interleukins and other well known growth factors.

Cells are introduced or reintroduced into the patient via standard techniques well known to those of skill in the art. For example, cells can be washed, suspended in, for example, buffered saline, and reintroduced into the patient via intravenous administration. The osteoclast precursor cells within the population of administered cells can rise to a subpopulation of cells which will differentiate into osteoclast cells. Such osteoclast cells will be capable of expressing a normal cathepsin K gene and/or a normal second gene, such as, for example, a normal cathepsin S gene, either endogenous or recombinant, thereby ameliorating osteosclerotic bone disorder symptoms.

5.4. METHODS FOR IDENTIFICATION OF COMPOUNDS FOR AMELIORATION OF BONE RESORPTION DISORDER-ASSOCIATED SYMPTOMS

A variety of methods can be utilized for identifying compounds capable of being used in ameliorating symptoms caused by bone resorption disorders, including but not limited to, osteoporosis, arthritides such as osteoarthritis, and periodontal disease, and damage caused by macrophage-mediated inflammatory processes.

The compounds identified via such methods are inhibitory compounds capable of specifically inhibiting cathepsin K activity and/or specifically inhibiting at least a second activity involved in bone resorption disorders and/or macrophage-mediated inflammatory damage processes. Such activities and specificities are as described, above, in e.g., Section 5.1. The identification methods described herein comprise isolated enzyme-based assays, cell-based assays and whole animal assays.

Enzyme-based assays can be utilized for rapid identification of specific inhibitory compounds. In general, such assays comprise contacting an enzyme to a model substrate for the enzyme, in the presence of a test compound for a time sufficient for the enzyme to act on the substrate. The level of substrate acted on by the enzyme is measured to determine the enzyme's level of activity. If the level of enzymatic activity observed in the presence of that compound is less then that observed in its absence, then that compound is considered an inhibitor of the enzyme. In order to determine whether the inhibitor is a specific inhibitor, the test compound is assayed with other enzyme/enzyme substrate pairs to determine whether it is inhibiting other enzymatic activities as well. If the test compound inhibits enzymatic activity of the first enzyme to a greater extent than it is inhibits activity of other agents of interest, the test compound is regarded as a specific inhibitor of the first enzyme.

Taking cathepsin K as an example, such as enzyme-based assay can include, first, contacting a model cysteine protease substrate with cathepsin K in the presence of a test compound for a time sufficient for cathepsin K to act on the substrate. The level of hydrolyzed substrate is then measured to determine cathepsin K enzymatic activity in the presence of test compound. The test compound is also tested in the presence of other individual cathepsin enzymes and the model cysteine protease substrate and the enzymatic activities of these individual additional cathepsins is also determined. If the test compound reduces the enzymatic activity of cathepsin K to a greater extent than it reduces the enzymatic activity of the other cathepsins, the test compound represents a cathepsin K specific inhibitor. Among the other cathepsins which can be measured are, for example, cathepsin S, B, L or H. Such an enzyme-based assay can also be utilized to identify specific inhibitors of another of the cathepsins which are measured. For example, a cathepsin S, B, L or H specific inhibitor can be identified via such an assay.

Such an enzyme-based assay can be expanded to further test the specificity of the inhibitor to test, for example whether it exhibits inhibiting action against other, non-cysteine protease enzymes, including, but not limited to serine proteases, metalloproteases and aspartyl proteases.

In cases where the inhibitor is contemplated for use in inhibition of cathepsin K and an additional activity, an inhibitor is also considered to be a specific inhibitor if it reduces the level of cathepsin K and the additional activity, for example, cathepsin S activity, to a greater extent than it reduces the other activity levels tested. The enzymes utilized in such assays will be in their active forms upon contacting with substrate and test compound. Taking cathepsin K as an example, a procathepsin K gene product can be isolated from a cell expressing a cathepsin K gene using standard cell expression, lysis and protein purification techniques well known to those of skill in the art. The isolated or partially isolated procathepsin K gene product can then be activated into cathepsin K. Conversion of the proform into the active enzyme form can be accomplished, for example, by treatment with pepsin as described, for example, in Bromme et al., 1996, J. Biol. Chem. 271:2126–2132, which is incorporated herein by reference in its entirety. Alternatively, procathepsin K can be heat activated in the presence of cysteine, as described by Bossard et al., 1996, J. Biol. Chem. 271:12517–12524, which is incorporated herein by reference in its entirety.

Substrates utilized for such enzyme-based assays should be ones whose cleavage, by hydrolysis, etc., by the enzyme of interest can readily be measured. For example, in the case of cathepsins, the substrates can be fluorogenic peptide substrates whose cleavage can be measured by standard fluorimetric methods. Among the cathepsin substrates which can be utilized are methylcoumarylamide (MCA) peptides. A substrate generally considered a model cysteine protease substrate is Z-Phe-Arg-MCA, where Z is carboxybenzyl. Cathepsin K favored substrates can also be utilized. For example, MCA peptides of the general structure $Z-P_3-P_2-P_1$-MCA (adapted from Bossard, M. J. et al., 1996, J. Biol. Chem. 271:12517–12524 and Bromme, D. et al., 1996, J. Biol. Chem. 271:2126–2132), where Z is carboxybenzyl, $P_1$ is preferably an amino acid residue having a hydrophilic side chain and $P_2$ is an amino acid having a small, hydrophobic side chain. In general, amino acid residues with hydrophobic side chains at the $P_1$ position are not favorable. In certain instances, such substrates can also act as enzyme inhibitors.

Collagen and/or osteonectin can also be utilized as cathepsin substrates in the identification methods of the invention. Such substrates can be labeled, for example, by utilizing standard techniques well known to those of skill in the art, in order to follow and measure their degradation.

It is further noted that certain substrates favorable to one cathepsin represent poor substrates for other cathepsin enzymes, which can be utilized as one means for identifying such cathepsin-specific inhibitors. For example, cathepsin K and cathepsin S enzymes exhibit similar substrate specificities. Both cathepsin K and cathepsin S, for example, recognize Z-Leu-Arg-MCA preferentially to Z-Phe-Arg-MCA, while cathepsin L exhibits an opposite preference. As another example, Z-Arg-Arg-MCA represents a poor cathepsin K, S and L substrate, but is readily recognized by cathepsin B.

Other differences between cathepsin K and other cysteine proteases such as, for example, cathepsin B and L, can be taken advantage of in identifying cathepsin K inhibitors. For example, cathepsin K exhibits an increased stability at neutral pH range. Further, cathepsin K exhibits an ability to efficiently hydrolyze Type I collagen and elastin at pH values above 6.0, and shows potent gelatinase activity in the pH range of 5–7, while cathepsin L, for example, is limited to a pH range of 4–5.5.

Among the test compounds which can be assayed for their specific inhibitory properties are, for example, peptidyl fluoromethyl ketones, vinyl sulfones, peptide aldehydes, nitriles, α-ketocarbonyl compounds, including, for example, α-diketones, α-keto esters, α-ketoamides, and α-ketoacids, halomethyl ketones, diazomethyl ketones, (acyloxy)-methyl ketones, ketomethylsulfonium salts and epoxysuccinyl compounds.

Among the methods for the identification of inhibitors as well as specific inhibitors, of cysteine protease enzymes are, for example, techniques described in Riese, R. J. et al., 1996, Immunity 4:357–366; Palmer, J. T. et al., 1995, J. Med. Chem. 38:3193–3196; Bromme, D. et al., 1996, J. Biol. Chem. 271:2126–2132; Bossard, M. J. et al., 1996, J. Biol. Chem. 271:12517–12524; WO 95/23222; U.S. Pat. No. 5,486,623; U.S. Pat. No. 5,525,623; U.S. Pat. No. 5,158,936; and U.S. Pat. No. 5,374,623, all of which are incorporated herein by reference in their entirety.

Compounds, including any of the compounds identified via the enzyme-based assays described above, can be tested in cell-based assays to test inhibitory capacity within the cell. Such cell-based assays can be utilized to test a number of features of a potential inhibitor, including, for example, the compound's ability to enter the cell, its cytoxicity, as well as its ability to act as an inhibitor once inside the cell. Further, cell-based assays can function to identify compounds which act more indirectly to inhibit enzyme activity by one or more of the activities listed, for example, in Section 5.1, above.

A typical cell-based assay involves contacting a cell expressing the activity of interest with a test compound for a time and measuring the inhibition of such an activity. For measurements, for example, whole cells can be lysed according to standard techniques and tested for the presence of various enzyme activities. Among preferred cell-based assays is ones such as that described in Riese et al. (Riese, R. J. et al., 1996, Immunity 4:357–366, which is incorporated herein by reference in its entirety).

Whole cell inhibitor assays can also be utilized. Such assays serve to test inhibitor capacity in an in vivo situation. Typically, such assays include administering to an animal a test compound and measuring its inhibitory effect. With respect to inhibitors of processes involved in bone resorption disorders, assays for inhibitory capacity can include, for example, standard measurements of hydroxyproline levels in urine and bone density measurements.

Any of the compounds identified via the techniques described herein can be formulated into pharmaceutical compositions as described above and utilized as part of the amelioration methods of the invention.

An inhibitor identified via the assay methods described herein can directly affect activity, such as, in this case, cathepsin K enzymatic activity, but can also alternatively act to suppress or inhibit cathepsin K gene expression. For example, inhibitor compounds can include, for example, specific inhibitors of cathepsin K gene transcription and/or translation. As discussed in Section 5.1.1, above, such gene expression inhibitors can include, but are not limited to, cathepsin K antisense and/or ribozyme inhibitors.

The specific inhibitors of a second activity involved in the bone resorption process which can be identified via the methods of the invention include, but are not limited to, inhibitors of a gene product involved in the biosynthesis, processing, activation, secretion, catalytic function, and/or stability of cathepsin K or cathepsin K gene expression; a gene product involved the availability or prior processing of the cathepsin K substrate(s) for hydrolysis by cathepsin K; another cathepsin, such as, for example, cathepsin S, L or B; a protein involved in the generation of active osteoclasts from their monocyte/macrophage progenitors; a protein involved in the function of osteoclasts such as, for example, in creating the acidic, sealed microenvironment of the sub-osteoclastic space; a regulatory gene that controls the tissue-specific upregulation of a protein involved in cathepsin K biosynthesis, processing, secretion, catalytic function, inhibition, or stability.

5.5. CATHEPSIN KNOCKOUT AND ANIMALS AND CELLS

Cells, cell lines and animals deficient for one or more cathepsin activities can be utilized, for example, as part of the identification specific inhibitor identification assays described above. For clarity, cathepsin K deficient cells, cell lines and animals will frequently be used herein as a representative example.

The term "cathepsin-deficient", as used herein, refers to cells, cell lines and/or animals which exhibit a lower level of functional cathepsin activity than corresponding cells, or cell lines or animals whose cells, contain two normal, wild type copies of the cathepsin gene. Preferably, "cathepsin-deficient" refers to an absence of detectable functional cathepsin activity.

A representative cathepsin-deficient, or "knockout" animal is a mouse cathepsin-deficient animal. Such animals are well known to those of skill in the art. See, for example, Horinouchi, K. et al., 1995, Nature Genetics 10:288–293; and Otterbach, B. & Stoffel, W., 1995, Cell 81:1053–1061, both of which are incorporated herein by reference in their entirety. Techniques for generating additional cathepsin knockout cells, cell lines and animals are described below.

Cells and cell lines deficient in cathepsin activity can be derived from cathepsin knockout animals, utilizing standard techniques well known to those of skill in the art. Such animals may be used to derive a cell line which may be used as an assay substrate in culture. While primary cultures may be utilized, the generation of continuous cell lines is preferred. For examples of techniques which may be used to derive a continuous cell line from the transgenic animals, see Small et al., 1985, Mol. Cell Biol. 5:642–648. Such techniques for generating cells and cell lines can also be utilized in the context of the transgenic and genetically engineered animals described below.

With respect to cathepsin K deficient cells, such cells can, for example, include cells taken from and cell lines derived from patients exhibiting osteosclerotic disorders, such as PYCNO, a disorder involving a cathepsin K deficiency. Additional cathepsin-deficient cells and cell lines can be generated using well known recombinant DNA techniques such as, for example, site-directed mutagenesis, to introduce mutations into cathepsin gene sequences which will disrupt cathepsin activity.

Cathepsin-deficient cells and animals can be generated using the cathepsin nucleotide sequences, for example cathepsin K nucleotide sequences, which are well known to those of skill in the art and/or which can routinely be isolated utilizing standard molecular biological techniques. Such animals can be any species, including but not limited to mice, rats, rabbits, guinea pigs, pigs, micro-pigs, and non-human primates, e.g., baboons, squirrel monkeys and chimpanzees.

Any technique known in the art may be used to introduce a transgene, such as an inactivating gene sequence, into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., U.S.A. 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

As listed above, standard embryonal stem cell (ES) techniques can, for example, be utilized for generation of cathepsin knockout and cathepsin-deficient animals. ES cells can be obtained from preimplantation embryos cultured in vitro (See, e.g., Evans, M. J. et al., 1981, Nature 292:154–156; Bradley, .O et al., 1984, Nature 309:255–258; Gossler et al., 1986, Proc. Natl. Acad. Sci. U.S.A. 83:9065–9069; Robertson et al., 1986, Nature 322:445–448; Wood, S. A. et al., 1993, Proc. Natl. Acad. Sci. U.S.A. 90:4582–4584.) The introduced ES cells thereafter colonize the embryo and contribute to the germ line of a resulting chimeric animal (Jaenisch, R., 1988, Science 240:1468–1474).

To accomplish cathepsin gene disruptions, the technique of site-directed inactivation via gene targeting (Thomas, K. R. and Capecchi, M. R., 1987, Cell 51:503–512) and review in Frohman et al., 1989, Cell 56:145–147; Cappecchi, 1989, Trends in Genet. 5:70–76; Barribault et al., 1989, Mol. Biol. Med. 6:481–492; Wagner, 1990, EMBO J. 9:3025–3032; and Bradley et al., 1992, Bio/Technology.

Further, standard techniques such as, for example, homologous recombination, coupled with cathepsin sequences, including cathepsin K nucleotide sequences, can be utilized to inactivate or alter any cathepsin genetic region desired. A number of strategies can be utilized to detect or select rate homologous recombinants. For example, PCR can be used to screen pools of transformant cells for homologous insertion, followed by screening of individual clones (Kim et al., 1988, Nucl. Acids Res. 16:8887–8903; Kim et al., 1991, Gene 103:227–233). Alternatively, a positive genetic selection approach can be taken in which a marker gene is constructed which will only be active if homologous insertion occurs, allowing these recombinants to be selected directly (Sedivy et al., 1989, Proc. Natl. Acad. Sci. U.S.A. 86:227–231). Additionally, the positive-negative approach (PNS) method can be utilized (Mansour et al., 1988, Nature 336:348–352; Capecchi, 1989, Science 244:1288–1292; Capecchi, 1989, Trends in Genet. 5:70–76). Utilizing the PNS method, nonhomologous recombinants are selected against by using the Herpes Simplex virus thymidine kinase (HSV-TK) gene and selecting against its nonhomologous insertion with herpes drugs such as gancyclovir or FIAU. By such counter-selection, the number of homologous recombinants in the surviving transformants is increased.

ES cells generated via techniques such as these, when introduced into the germline of a nonhuman animal make possible the generation of non-mosaic, i.e., non-chimeric progeny. Such progeny will be referred to herein as founder animals. Once the founder animals are produced, they may be bred, inbred, outbred, or crossbred to produce colonies of the particular animal.

Taking as an example of the above, the generation of a cathepsin K knockout mouse, first, standard techniques can be utilized to isolate mouse cathepsin K genomic sequences. Such sequences can be routinely isolated by utilizing standard molecular techniques and human cathepsin K nucleotide sequences as probes and/or as PCR primers, as discussed below.

An inactive allele of the cathepsin K gene can then be generated by targeted mutagenesis using standard procedures of combined positive and negative selection for homologous recombination in embryonic stem (ES) cells. Cathepsin K genomic clones can be isolated, for example, from a 129/sv mouse genomic library, which is isogenic with the W9.5 line of ES cells to be used for gene targeting. The null targeting vector can be constructed containing homologous sequences flanking both 5' and 3' sides of a deletion of the first coding exon (exon 2), including the translational initiation codon, and other essential coding sequences of the gene. The vector carries a resistance marker, e.g., a neomycin resistance marker (Neo) for positive selection and a negative marker, e.g., a thymidine kinase (TK) marker, for negative selection. Vectors can be utilized which are analogous to previously reported targeting vectors, successfully used for generating knock-out mice for other genes, e.g., for Niemann-Pick Disease, NMDA receptor and thyroid hormone receptor.

Briefly, vector DNA can be electroporated into W9.5 ES cells (male-derived), which can then be cultured and selected on feeder layers of mouse embryonic fibroblasts derived from transgenic mice expressing a Neo gene. G418 (350 mg/ml; for gain of Neo) and ganciclovir (2 mM; for loss of TK) can be added to the culture medium to select for resistant ES cell colonies that have undergone homologous recombination at the URO-D gene. Recombinants are identified by screening genomic DNA from ES cell colonies by Southern blot hybridization analysis. Correctly targeted ES cell clones, which also carry a normal complement of 40 chromosomes, can be used to derive mice carrying the mutation. ES cells can be micro-injected into blastocysts at 3.5 days post-coitum obtained from C57BL/6J mice, and blastocysts will be re-implanted into pseudopregnant female mice, which serve as foster mothers. Chimeric progeny derived largely from the ES cells will be identified by a high proportion of agouti coat color (the color of the 129/sv strain of origin of the ES cells) against the black coat color derived from the C57BL/6J host blastocyst. Male chimeric progeny will be tested for germline transmission of the mutation by breeding with C57BL/6J females. Agouti progeny derived from these crosses will be expected to be heterozygous for the mutation, which will be confirmed by Southern blot analysis. These F1 heterozygous progeny will be inter-bred to generate F2 litters containing progeny of all three genotypes (wild type, heterozygous and homozygous mutants) for phenotypic analyses.

Once such a cathepsin K mouse is generated, it would be possible to also generate doubly or multiply cathepsin-deficient animals by, for example, beginning with cells derived from the cathepsin K animal and repeating the above procedures utilizing a second cathepsin, for example, cathepsin S, gene sequence for inactivation.

5.6. BONE DENSITY AND CATHEPSIN K POLYMORPHISMS/MUTATIONS

It is contemplated that polymprphisms and/or mutations within the cathepsin K gene can affect bone density in individuals carrying alleles containing such polymorphisms and/or mutations. Methods are presented herein for the detection of bone density affecting polymorphisms within the cathepsin K gene.

In general, such methods comprise the correlation of specific polymorphisms and/or mutations of classes of such polymorphisms and/or mutations with a specific bone density phenotypic range. By detecting individuals exhibiting or predisposed to bone density-related disorders, appropriate therapeutic or prophylactic treatments can be prescribed. Further, by determining the expected severity of the bone density disorder generally associated with a specific genotype, more treatments can be administered which are more commensurate with the severity or expected severity of the bone density disorder.

First, bone density measurements can be performed on an individual to be tested, for example, an individual in a risk group for a bone density disorder such as osteoporosis. Such bone density measurements are well known to those of skill in the art. For example, dual energy X-ray absorptimetry (DEXA) measurements can be performed to assay bone mineral density. See, e.g., Sim, L. H. and Doorn, T., 1995, Austral. Phys. Eng. Sci. Med 18:65–80.

Next, cathepsin K polymorhisms and/or mutations can be detected in the individual being tested, using standard techniques which are, as described below, well known to those of skill in the art. Upon measuring both bone density and cathepsin K polymorhisms, a correlation between bone density and the specific cathepsin K allele(s) present in the individual can be assessed and compared. Within a population of individuals, it can be possible to correlate a given bone density with a given cathepsin K polymorphism. In certain instances, the presence of a given polymorphism may so tightly correlate with a given bone density that it may become possible to carry out only the cathepsin K polymorphism analysis, in the absence of the bone density measurements.

Mutations within the cathepsin K gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving cathepsin K gene structure, including point mutations, insertions, deletions and chromosomal rearrangements. Such assays may include, but are not limited to, Southern analyses, single stranded conformational polymorphism analyses (SSCP), and PCR analyses, all of which are well known to those of skill in the art. The cathepsin K gene sequences which can be used can include, for example, cathepsin K cDNA (see, e.g., Shi, G. P. et al., 1995, FEBS Lett. 357:129–134). Further, the cathepsin K sequences which can be utilized can include the cathepsin K genomic sequences disclosed herein. Still further, the cathepsin K genomic structure, presented here for the first time, can be utilized in analyzing the cathepsin K polymorphisms and/or mutations present in a given individual to be tested.

6. EXAMPLE: LOSS OF CATHEPSIN K ACTIVITY IS THE CAUSATIVE AGENT OF PYCNODYSOSTOSIS

The Example presented herein demonstrates the discovery for the first time, of an agent which degrades bone matrix in vivo. Specifically, this Example demonstrates that loss of cathepsin K activity is responsible for pycnodysostosis, (PYCNO) an autosomal recessive osteochondrodysplasia characterized by osteosclerosis and short stature. The findings thus define cathepsin K as a major protease involved in matrix degradation, as exemplified here by osteoclast-mediated matrix degradation associated with bone resorption.

6.1 MATERIALS AND METHODS

Cathepsin S exons 2–5 were amplified from genomic DNA and sequenced by cycle sequencing using an ABI 377 sequencer. For analysis of the remaining coding region, total lymphoblast RNA was extracted (RNazol, Tel Test) and first-strand CDNA was synthesized using an oligo dT primer (Gibco BRL). Cathepsin S CDNA nucleotides 631–1231 were amplified using gene-specific primers. Sequence comparisons were carried out with the AutoAssembler software package (Applied Biosystems)

The R113W substitution in the cathepsin S gene was assessed in genomic DNA by amplification of a 150 bp product containing exon 4 and the adjacent intron 4 sequence using the antisense (5'-GCATTTAAAGAGCTCTACCTAGGGTT-3'(SEQ ID NO: 6)) and the sense (5'-CAGAGAAATATCACATATAAGTCAAACCC CAAT-3'(SEQ ID NO: 7)) primers, the latter introduced a T-to-C change (underlined) that created a MunI restriction site in the allele with the sequence variation. The amplified product was isolated (Qiagen), digested and analyzed on a 2% agarose gel.

Cathepsin S enzymatic activity was assayed in lymphoblast lysates fluorometricly using the substrate Z-Val-Val-Arg-NHMec (Bachen Feinchemikalien AG, Bubendorf, Switzerland) following inactivation of cathepsins B, L, and H at 40° C. (Kirschke, H. and Wiederanders, B., 1994, Methods in Enzymology: 244:500, Academic Press, New York). The control lysosomal enzyme, α-galactosidase A, was determined fluorometrically (D. Bishop, F. and Desnick, R. J. 1982, J. Biol. Chem. 256, 1307).

Cathepsin K cDNA was amplified by RT-PCR from PYCNO lymphoblast total RNA. For PCR amplification, cathepsin K sense and antisense primers were synthesized corresponding to the 5' and 3' untranslated regions (5'-GCCGCAATCCCGATGGA-3'(SEQ ID NO: 12) and 5'-CCTTGAGGATATTGAAGGGAACTTAG-3'(SEQ ID NO: 13), respectively). Nested sense and antisense PCR primers (5'-CCCCTGATGGTGTGCCCCA-3'(SEQ ID NO: 14) and 5'CCCTTCCAAAGTGCATCGTTACACT-3'(SEQ ID NO: 15), respectively) were used to reamplify the cathepsin K cDNA from the initial PCR product. Products were isolated and cycle sequenced in both orientations.

The putative cathepsin K mutation in the affected Israeli Arab PYCNO patients was assayed in family members and in unrelated normal Arab individuals by amplifying nucleotides 998–1170 from genomic DNA using flanking primers (5'GGGGAGAAAACTGGGGAAACA-3'(SEQ ID NO: 16) and the antisense primer from the nested PCR) and then digesting with HinfI (New England Biolabs).

6.2 RESULTS

In an initial attempt to identify the PYCNO gene, a genome-wide search for the PYCNO locus was undertaken in a large, consanguineous Israeli Arab family with 16 affected relatives (Gelb, B. D. et al., 1995, Nature Genet. 10:235). A genomic region that was homozygous-by-descent for all affected individuals was localized to the pericentric region of chromosome I with a lod score of 11.72 at D1S498. Ancestral recombinant events localized the PYCNO region to 4 cM from D1S442 to D1S305 (FIG. 1).

Independent linkage analysis of a large Mexican PYCNO family confirmed linkage to the pericentric region of chromosome I and excluded the macrophage colony stimulating factor, CSF1, which is defective in the op/op mouse model of osteopetrosis (Polymeropoulos, M. H. et al., 1995, Nature Genet. 10:238). Recently, the PYCNO locus was narrowed to a region of about 2 cM at chromosome 1q21 from D1S2344 to D1S2343/D1S2345 by analyzing the Israeli Arab family with new markers (Gelb, B. D. et al., 1996, Hum. Genet. 98:141–144; FIG. 1). This refinement excluded the interleukin-6 receptor gene which previously had been proposed as a candidate gene (Gelb, B. D. et al., 1995, Nature Genet. 10:235), but included, for example, MCL1, a Bc12 homolog relevant to monocyte/macrophage differentiation.

An additional putative candidate gene was lysosomal cathepsin S, a cysteine protease with expression in osteoclasts which had been assigned to chromosome band 1q21 by FISH analysis (Shi, G.-P., et al., 1994, J. Biol. Chem. 269:11530). To determine whether cathepsin S mapped to the PYCNO critical region, a cathepsin S sequence tagged site (STS) was developed using the published 5'-flanking region sequence (Shi, G.-P., et al., 1994, J. Biol. Chem. 269:11530), and STS content mapping was performed with a yeast artificial chromosome (YAC) contig spanning the PYCNO region utilizing standard techniques. The cathepsin S STS was amplified from two overlapping CEPH megaYACs, 978e4 and 947e1, and was mapped centromeric to D1S498 in the PYCNO critical region (FIG. 1).

Sequencing of the cathepsin S coding region in affected members from the Israeli Arab family and from a consanguineous Moroccan Arab family by exon amplification from genomic DNA and by RT-PCR revealed a C-to-T transversion of a CpG dinucleotide at position 343 in the cDNA in both families, predicting an R113W substitution in the propeptide,near the putative cleavage site at I114 (Shi, G.P. et al., 1992, J. Biol. Chem. 267:7258).

Analysis of 18 unrelated normal Israeli Arab individuals living near the Israeli Arab PYCNO family demonstrated that 12 of 36 alleles were positive for R113W, consistent with it being a sequence polymorphism. In addition, cathepsin S activities in lymphoblasts from two Israeli Arab PYCNO patients and three normal controls were not significantly different (210 Mu/U α-gal A±100 vs 340±40, respectively) Thus, cathepsin S was ruled out as a candidate gene for PYCNO.

Although cathepsin S was ruled out by these studies as a candidate gene for PYCNO it was determined, for the first time, that another cathepsin cysteine protease, cathepsin K, also mapped to the critical 1q21 region. This determination was made via chromosomal fluorescence-labeled in situ hybridization (FISH), using a labeled cathepsin K primer and standard techniques, and also by an amplification study.

For the amplification study, a cathepsin K STS, developed from the published 3' cathepsin K untranslated region (Shi, G.-P. et al., 1995, FEBS Letters 357:129; Bromme, D. & Okamoto, K., 1995, Biol. Chem. Hoppe-Seyler 376:37; Tezuka, K., et al., 1994, J. Biol. Chem. 269:1106; Inaoka, T., et al., 1995, Biochem. Bioshys. Res. Commun. 206:89), was amplified from the same two overlapping YACs in the PYCNO critical region that contained the cathepsin S STS. RT-PCR amplification and sequencing of the cathepsin K transcript from lymphoblast total RNA derived from two Israeli Arab PYCNO patients revealed an A-to-G transition at cDNA nucleotide 1095 (Shi, G.-P. et al., 1995, FEBS Letters 357:129; Bromme, D. & Okamoto, K., 1995, Biol. Chem. Hoppe-Seyler 376:37; Tezuka, K., et al., 1994, J. Biol. Chem. 269:1106; Inaoka, T., et al., 1995, Biochem. Bioshys. Res. Commun. 206:89.), which predicted the substitution of the termination codon by a tryptophan residue (X330W) and the elongation of the carboxy-terminus by 19 additional amino acids (FIG. 2).

Evaluation of the X330W allele in the entire Israeli Arab PYCNO family and 43 unrelated normal Arab control individuals revealed that it cosegregated with disease in the PYCNO family and was not present in any of the 86 Arab control alleles. Further evidence that cathepsin K mutations caused PYCNO was the finding of five additional mutations, yielding a total of eight cathepsin K mutations within twelve PYCNO families (FIG. 2). For example, two affected Moroccan Arab siblings had a missense mutation, a G-to-C transversion at nucleotide 541, predicting a G146R substitution. Further, an American Hispanic patient with non-consanguineous parents was found to be heterozygous for markers across the PYCNO critical region. Sequence analysis demonstrated heteroallelism for the G146R mutation and a C-to-T transition of a CpG dinucleotide at nucleotide 826, predicting an R241X nonsense mutation. Restriction analysis of amplified segments from genomic DNA with BanI for G146R and AvaI for R241X confirmed the RT-PCR results. In addition, a nonsense mutation, K52X, which predicts a severely truncated protein, and E79G, a missense mutation, were both found in a heterallelic form in a patient from a Utah family. Further, the R241X and the missense mutation Y212C was a found in patients from a Spanish PYCNO family. The Spanish family contained two PYCNO patients from different generations, with the older patient being homoallelic and the younger heterallelic. Two additional missense mutations, A277E and R 321G, were found in families as indicated in FIG. 2. See FIG. 2 for a complete summary or which alleles have been found in the particular families.

To assess the effects of the putative Israeli Arab cathepsin K mutation on enzyme activity, the X330W mutation was introduced by site-directed mutagenesis into the full-length cDNA. The normal and X330W cathepsin K alleles were transiently expressed in 293 cells which do not have detectable cathepsin K protein (FIG. 3A). Cathepsin K protein was observed by immunoblotting in the whole cell lysates of cells transfected with the nominal allele. In contrast, no detectable protein was observed in lysates from cells transfected with the X330W construct. Northern analysis of total RNA from transfected cells revealed comparable steady-state transcript levels between normal and mutant for both cathepsin K and the co-transfected adenovirus-associated I RNA gene (FIG. 3B).

The cathepsin K X330W mutation altered the stop codon and predicted an elongated polypeptide. Such mutations are rare, the best characterized being Hb Constant Spring which results in an unstable transcript, thereby decreasing α globin chain synthesis (Clegg, B. et al., 1971; Nature 234:337; Rousseau, F. 1995, Nature Genet. 10:11–12; Liebhaber, S. A. & Kan, Y. W. 1981, J. Clin. Invest. 68:439; Hunt, D, M. et al., 1982, Br. J. Haematol. 51:405–413). In contrast, the X330W cathepsin K polypeptide was not detected in transfected cells despite normal transcript levels, suggesting protein instability. The R241X mutation predicts truncation of the polypeptide at residue 241, and the loss of 89 amino acids including the completely conserved H276 and N296 residues of the active site (Shi, G.-P. et al., 1995, FEBS Letters 357:129; Bromme, D. & Okamoto, K., 1995, Biol. Chem. Hoppe-Seyler 376:37; Tezuka, K., et al., 1994, J. Biol. Chem. 269:1106; Inaoka, T., et al., 1995, Biochem. Bioshys. Res. Commun. 206:89.). In addition, truncation mutations are known to cause transcript instability and degradation and also can result in exon skipping (Dietz, H. C. et al., 1993, Science 259:680), while the K52X mutation predicts an even more severly trucated protein. Thus, the R241X and K52X mutation, are presumably null for cathepsin K activity. Further, each of the missense mutations cause significant changes in amino acid residue types at the affected positions, which can affect activity.

Little, if any, cathepsin K activity is detectable in lymphoblasts or fibroblasts, limiting the laboratory diagnosis of RT-PCR to DNA-based methods. As shown by these studies, specific cathepsin K mutations causing PYCNO can be detected by RTPCR and sequencing of transcripts from lymphoblasts. The cathepsin K gene organization shown in FIG. 2 and discribed below, in Section 8, will facilitate direct mutation analysis from genomic DNA That PYCNO results from mutations in the cathepsin K gene is notable. This pure skeletal dysplasia is now classified as a lysosomal disease, resulting from the deficient activity of a lysosomal protease. Most lysosomal enzymes are constitutively expressed in all cell types (except erythrocytes) and lysosomal disease phenotypes result from the accumulation of their substrate(s) in various cells and tissues. For example, the mucopolysaccharidoses and most glycoproteinoses each has diverse manifestations such as dysostosis multiplex, mental retardation, corneal dystrophy, and hepatosplenomegaly. In contrast, the PYCNO phenotype, which is restricted to bone, results from the deficiency of an enzyme required for bone resorption by osteoclasts with minimal storage of its substrate. The cell-specific high expression of cathepsin K is unique among known lysosomal enzymes defining PYCNO as a lysosomal disorder due to defective tissue-specific expression.

Recently, cysteine proteases have been implicated in bone resorption and remodeling based on the immunohistologic localization of cathepsins B and L to the subosteoclastic space (Blair, H. C. et al., 1993, Clin. Orthop. 294:7; Goto, T., 1994, Histochemistry 101:33), and by the in vitro inhibition of bone matrix degradation using non-specific cysteine cathepsin inhibitors (Debari, K. et al, 1995, Calcif. Tissue Int. 56:566; Everts, V. et al., 1988, Calcif. Tissue Int. 43:172; Everts, V. et al., 1992, J. Cell. Physiol. 150:221; Kakegawa, H. et al., 1993, FEBS Letters 321:247). The finding that cathepsin K deficiency causes PYCNO, taken together with the knowledge that cathepsin K is the only cysteine protease highly expressed in osteoclasts (Shi, G.-P. et al., 1995, FEBS Letters 357:129; Bromme, D. & Okamoto, K., 1995, Biol. Chem. Hoppe-Seyler 376:37; Tezuka, K., et al., 1994, J. Biol. Chem. 269:1106; Inaoka, T., et al., 1995, Biochem. Bioshys. Res. Commun. 206:89) and that it has the highest type I collagenolytic, elastinolytic, and gelatinolytic activities of cysteine proteases (Bromme, D. et. al., 1996, J. Biol. Chem. 271:2126), indicates that cathepsin K is the major protease in bone matrix resorption.

7. EXAMPLE: CATHEPSIN K MUTATIONS INDICATE PRESENCE OF COMMON NON-CATHEPSIN PYCNO PREDISPOSING MUTATIONS

The Example presented in Section 6, above, demonstrated the definitive identification of the loss of cathepsin K activity to be the cause of the bone disorder, PYCNO. The Example presented in this Section presents surprising data that indicate the presence of a second common polymorphism or mutation in a second gene which leads to a predisposition for PYCNO.

First, in a study of four presumably related families on Madeira Island, Portugal, a small island with a population of approximately 250,000 at least three separate cathepsin K mutations were found in PYCNO individuals, PYCNO being a disorder with a incidence of less than one in a million. This finding suggested that a second gene locus with a more common, even frequent, mutation contributed to the deficient bone resorption causing PYCNO among these Portuguese patients. Thus, five Portuguese PYCNO patients had four different cathepsin K mutations. This is remarkable, particularly since four of the families were individually consanguineous and their affected members were homoallelic for each of the four mutations and any closely linked genes.

The concept of a predisposing polymorphism or mutation in a second gene is supported by two findings. First, a total of 16 presumably unrelated families with PYCNO have been analyzed for cathepsin K mutations. In each family, all affected members within families inherited the same cathepsin K mutation inherited as an autosomal recessive trait. Of these 16 families whose collection was based mostly on previous case reports, nine or about 60% were of Hispanic ancestry, suggesting a common predisposing polymorphism or mutant gene, at least in the Hispanic patients. Also, the family reported by Polymeropoulos, supra., was of Mexican ancestry. Other such predisposing polymorphisms may occur in other ethnic, demographic, or inbred groups. Such a predisposing gene would cause PYCNO when cathepsin K activity was also deficient.

The second finding is based on an analysis of a large Israeli Arab family, referred to above, in Section 6. PYCNO inheritance in this family tracks perfectly with the cathepsin K genetic region, suggesting that the second gene might lie in the same immediate region of chromosome position 1q21. As discussed in Section 6, above, this region had already been shown to contain cathepsin S and K. The region could further contain additional cathepsins or other relevant genes.

The analysis revealed a mutation (R113W) in the cathepsin S gene, another cysteine protease gene located adjacent (<150 kb) to the cathepsin K gene on chromosome band 1q21. As discussed above, in Section 6, both the cathepsin K and S genes, mapped to the PYCNO critical region between D1S2344 and D1S2343/D1S2345. Further, both genes were found to be present on the same human PAC (P1 artificial chromosome; clone 74e16). The cathepsin S mutation was inherited in the homozygous condition by all affected members of the Israeli Arab family. It should be noted that the R113W mutation may be involved in the processing of the cathepsin S polypeptide to a functionally active form. It should further be noted that the cathepsin S mutation was common, occurring in about one-third of the Arab population living in the same area of Israel as the affected family. Thus, the expression of this disease may require alteration in at least two genes, perhaps adjacent, as in the case of cathepsins K and S in the Israeli Arab family.

This finding bears directly on the treatment of disorders due to excessive bone resorption. If inhibitors of cathepsin K are proposed to treat osteoporosis, the effects of such interventions may depend on the nature of the polymorphism or mutation in the second (or additional) predisposing gene(s). For instance, if there is a second cathepsin with overlapping function in bone resorption, an inhibitor of cathepsin K the minimal affects on this second cathepsin might be ineffective, whether the two cathepsins work independently, dependently, or synergistically. Thus, the presence of a second, presumably closely-linked locus involved in the synthesis, processing, function, or transport of cathepsin K, or directly in the bone resorption process, is highly relevant to interventions in the bone resorption process.

It is notable that another genetic disorder (limb-girdle muscular dystrophy Type 2A) caused by the deficiency of a neutral cysteine protease, calpain 3, was recently identified in which presumably related families on a small island had different mutations (Richard, I et al., 1995, Cell 81:27–40). Calpain 3 belongs to a family of calpains, analogous to the cathepsin family. The finding of multiple mutations in Calpain 3 suggested to Richard et al. that a "digenic" model in which only in the presence of specific alleles at a permissive second locus (e.g., a compensatory, partially redundant, regulatory, or modifier gene) will there be expression of calpain mutations. Since one would need mutations at both loci to be affected, the disease prevalence would remain low. By analogy, it is possible that a similar situation holds for cathepsin K, that another locus, perhaps a cathepsin like S, is required for expression of the disease. Therefore, it may require inhibitors of both genes or enzymes to prevent or inhibit bone resorption.

8. EXAMPLE: CATHEPSIN K GENOMIC STRUCTURE

In this Example, the genomic organization of the cathepsin gene is presented, including the exon and intron sizes, the exon/intron boundary sequences, the transcription initiation site and the 5' flanking region. In addition, the chromosomal location of the gene was determined by fluorescence in situ hybridization (FISH). The isolation and dissection of the cathepsin K genomic structure is especially advantageous, given the fact that cathepsin K cDNA-based analyses are quite difficult utilizing standard techniques. Specifically, the lymphoblast blood cells usually isolated for studies such as diagnostic analyses are virtually devoid of cathepsin K RNA, making these standard cells a poor cDNA starting source.

To isolate a genomic clone containing the cathepsin K gene, a human PAC library (Genome Systems, St. Louis, Mo.) was screened by PCR using a cathepsin K sequence tagged site (STS) from the 3' untranslated region (UTR). PAC DNA from the positive clone, 74e16, was isolated by standard methods. Using the genomic organization data from cathepsins S and L (Shi, G. P. et al., 1994, J. Biol. Chem. 269:11530–11536), probable sites for exon-intron boundaries in the cathepsin K cDNA were selected. The seven predicted introns were PCR amplified from either human genomic or PAC 74e16 DNA with exonic oligonucleotides. The amplified products were sized on an agarose gel and cycle sequenced on an ABI 377 sequencer. The genomic sequence was divided into eight exons ranging from 103 to 665 nt (FIG. 4). Exon 2 contained the translation initiation site, all codons for the signaling prepeptide and a portion of the propeptide, exon 4 encoded the C-terminus of the propeptide and the N-terminus of the mature enzyme, and exon 8 contained the stop codon. The seven introns ranged in size from 86 nt to 2.4 kb, the entire gene being approximately 9 kb.

As shown in Table 1, (SEQ ID NOS:13–20, corresponding to 5' splicing sites; SEQ ID NOS: 21–28, corresponding to 3' splicing sites), below, the exon/intron boundary sequences conformed to the GT/AG rule with a single exception (Shapiro, M. B. and Senapathy, P., 1987, Nucl. Acids Res. 15:7155–7174). The 5' splicing donor site of exon 3 was non-conforming, containing the sequence TGgc, a pattern observed in approximately 1% of these sites. The boundary sequences were generally consistent with the 5' and 3' splice consensus sequences. Variations from the consensus sequences were all permissible for the primate exon/intron boundary sequences.

TABLE 1

Exon/Intron Boundaries of the Human Cathepsin K Gene

| Exon number and (size) (nt) | cDNA position of exon | 5' Splicing site | Intron number and (size) (kb) | 3' Splicing site | Codon Phase |
|---|---|---|---|---|---|
| 1 (103) | -104--2 | TCAGCAG gtaacg | 1 (1.2) | ctgtttccctgccaaatggaagagttttccctaactacattcttctgcag GATGTGGGG | II |
| 2 (122) | -1-121 | CAACAAG gtgcct | 2 (0.463) | catatgtaactgtagacagtctatacaagtactgactatgctttgtttag GTGGATGAA | I |
| 3 (123) | 122–244 | GGACATG gcaagt | 3 (0.086) | atttgctttagttccctgctgatgcctggcctctttcttctttgtcttag ACCAGTGAA | I |
| 4 (156) | 245–400 | AAATCAG gtactc | 4 (1.5) | atagaaaatgtaaacagcaaagattgatagttttctctgtatgcctttcag GGTCAGTGT | I |
| 5 (219) | 401–619 | GGGACAG gtgaga | 5 (0.64) | tcattgcctattgctttgtcctagtcctattacaatcttgtttcttccag GAAGAGAGT | I |
| 6 (166) | 620–785 | AGCAAAG gtaaga | 6 (0.270) | gggtgacccttggattgcatagagcctcacgctggtagtttgtattctag GTGTGTATT | III |
| 7 (106) | 786–891 | AAAACAG gtaatg | 7 (2.4) | tgaataaataaactgagagtactaagtattttcttgattggtcttacag CTGGGGAGA ttttttctttncag G | II |
| 8 (665) | 892–1556 | <sup>A</sup>AG gt<sup>a</sup><sub>g</sub>agt | | | |

Consensus sequence: donor: <sub>c</sub>    acceptor: ccccccctccc

To determine the cathepsin K transcription initiation site, primer extension analysis was performed using a cathepsin K-specific antisense oligonucleotide primer which was end-labeled with [$^{32}$P]-γ-ATP using T4 polynucleotide kinase. Either human brain total RNA or human lung mRNA was used with the radiolabeled primer for the reverse transcription reaction. The primer extension experiments were carried out as previously described (Shi et al., supra). Three bands, corresponding to positions −169, −102, and −40, were identified (FIG. 5).

The 5' flanking region for the cathepsin K gene was subcloned into pGEM4z from PAC 74e16 after Nsi I digestion and identified by colony hybridization with an end-labeled exon 1 oligonucleotide. Comparison of this 5' flanking sequence cloned with the 5' UTRs from the cathepsin K cDNAs revealed sequence divergence (FIG. 3). The 18 nt 5' UTR from the osteoclastoma cathepsin k cDNA (Li, Y.-P. et al., 1995, J. Bone Miner. Res. 10:1197–1202) matched all other sequences, and is presumed to represent a partial transcript. The 5' UTR of a macrophage-derived cDNA (Shi, G. P. et al., 1995, FEBS Lett. 357:129–134) was 105 nt in length and matched the genomic sequence, nearing the transcription start site at −40. Its first 12 nt did not match and presumably represents a cloning artefact. The cathepsin K 5' UTR cloned from arthritic bone (Inaoka, T. et al., 1995, Biochem. Biophys. Res. Commun. 206:89–96) showed identity with 46 nt of exon 1 but its first 84 nt did not match the genomic sequence. Sequence comparison of these 84 nt revealed complete identity with the cathepsin K coding sequence at nt 864–876 and the reverse complement of 786–856. Interestingly, this corresponded to the 5' boundary of exon 7, suggesting that this 5' UTR sequence was not an cloning artefact but rather an error in transcription and/or message splicing.

In contrast, the 141 nt 5' UTR from a spleen cathepsin K cDNA clone reported by Bromme and Okamoto (Bromme, D. et al., 1995, Biol. Chem. Hoppe-Seyler 376:379–384.) was identical to 100 nt of exon 1, ending at the −102 transcriptional start site, but failed to match the genomic sequence at its most 5'40 nt (FIG. 6). BLASTn searching of the non-redundant sequence and dbEST databases with these 40 nt matched only self. To determine the authentic 5' sequence, sense oligonucleotides, corresponding to this 5' UTR and to the predicted sequence near the transcription initiation site (primer CTSK43 in FIG. G), and an antisense primer in exon 2 were used to PCR amplify the 5' UTR from human brain and lung randomly primed first-strand cDNAs. A product of the predicted size was amplified using the primer matching the genomic sequence, but no product was amplified using the primer based on the Bromme-Okamoto 5' UTR. These results demonstrated that the 5' flanking region shown in FIG. 6 is the major, and perhaps only, promoter in lung and brain. Since the relevant portions of cathepsin K cDNA clones from bone and osteoclastomas showed sequence identity with exon 1, this 5' flanking region is likely the promoter controlling expression of cathepsin K in osteoclasts as well.

Analysis of the genomic sequence upstream from the transcription initiation site revealed a rather featureless promoter which lacked the canonical TATA and CAAT box sequences. Promoters from other members of the papain family of cysteine proteinases, cathepsins S and B, have also lacked TATA boxes (Gong, Q., et al. 1993, DNA Cell Biol. 12:299–309; Shi, G. P. et al., 1994, J. Biol. Chem. 269:11530–11536). The cathepsin K promoter contained two AP1 sites at −315 and −346, was not particularly GC rich and lacked SP1 sites. This promoter was similar to the cathepsin S promoter which contained multiple AP1 sites and few SP1 sites but contrasted with the cathepsin B promoter which was GC rich and contained 15 SP1 sites, corresponding well with the fact that both cathepsins K and S are highly regulated while cathepsin B is expressed constitutively. The signals which regulate cathepsin K expression are not known. Since the principal role for cathepsin K is in bone remodeling, putative estrogen response elements were specifically sought in this genomic sequence but none was found. Such elements have been identified further upstream in promoters or in introns in other estrogen-responsive genes (Sohrabji, F., et al., 1995, Proc. Natl. Acad. Sci. U.S.A. 92:11110–11114), indicating a possible role of estrogen in regulating the expression of cathepsin K in osteoclasts.

The chromosomal localization of the cathepsin K gene was identified by FISH. Purified human cathepsin K cDNA was labeled with biotin 11-dUTP (Gibco BRL, Gaithersburg, Md.) by nick translation and hybridized to human metaphase chromosomes from two normal males as previously described. Probe signals were were detected with avidin-fluorescein antibody (X,X) and chromosomes were stained with 4,6-diamidino-2-phenylindole dihydrochroride (DAPI; Oncor, Gaithersburg, Md.). Among the 22 metaphases scored, hybridization signal was observed at chromosome band 1q21 from one or both chromatids in 21. Since cathepsin S had also been mapped to 1q21 by FISH (Shi, G. P. et al. 1994, J. Biol. Chem. 269:11530–11536), the possibility was considered that cathepsins K and S might reside in tandem. Indeed, STSs for both cathepsin K and S were amplified from PAC 74e16 by PCR. Since PAC insert sizes range from 100–150 kb, these two cathepsin genes, each approximately 10 kb in length, lie in close proximity to one another.

In summary, the cathepsin K gene was localized to within 150 kb of cathepsin S on chromosome 1q21. Like cathepsins S and L with which it is highly homologous, the cathepsin K genomic structure comprised 8 exons that were interrupted by introns in the same coding sequence, suggesting that all three genes evolved from a common ancestral cysteine proteinase gene. Three transcription initiation sites were identified at nt−164, −102, and −40 human brain and lung. Analysis of the 5' flanking region, believed relevant for the high expression in osteoclasts, revealed a TATA-less promoter with two AP1 sites. The knowledge of the cathepsin K genomic structure will, for example, facilitate mutation analysis in pycnodysostosis patients and further studies of the evolutionary relatedness of the lysosomal cysteine protease genes.

---

What is claimed is:

1. A method for ameliorating bone resorption disorder symptoms, comprising: contacting a compound capable of specifically inhibiting cathepsin K activity to an osteoclast for a time sufficient to inhibit the cathepsin K activity of the osteoclast so that symptoms of the bone resorption disorder are ameliorated.

2. The method of claim 1, further comprising: contacting a second compound to the osteoclast, wherein the second compound is capable of specifically inhibiting a second bone resorption activity, for a time sufficient to inhibit the cathepsin K and the second activity of the osteoclast so that symptoms of the bone resorption disorder are ameliorated.

3. The method of claim 1, wherein the compound further inhibits a second bone resorption activity.

4. The method of claim 2 wherein the second activity is cathepsin S activity.

5. The method of claim 3 wherein the second activity is cathepsin S activity.

* * * * *